(12) United States Patent
Shin et al.

(10) Patent No.: US 9,945,772 B2
(45) Date of Patent: Apr. 17, 2018

(54) METHOD OF MEASURING AN ADHESIVE FORCE OF INTERLAYER ADHESIVE LAYER IN TENSILE MODE FOR STACKED SEMICONDUCTOR DEVICE AND APPARATUS FOR MEASURING THE SAME

(71) Applicants: SK hynix Inc., Icheon (KR); Industry-Academic Cooperation Foundation, Yeungnam University, Gyeongsan (KR)

(72) Inventors: Dong Kil Shin, Hwaseong (KR); Chul Keun Yoon, Suwon (KR); Min Kyu Kang, Seoul (KR); Gyu Jei Lee, Seoul (KR)

(73) Assignees: SK HYNIX INC., Icheon (KR); INDUSTRY-ACADEMIC COOPERATION FOUNDATION, YEUNGNAM UNIVERSITY, Gyeongsan (KR)

( * ) Notice: Subject to any disclaimer, the term of this patent is extended or adjusted under 35 U.S.C. 154(b) by 220 days.

(21) Appl. No.: 15/002,215

(22) Filed: Jan. 20, 2016

(65) Prior Publication Data
US 2016/0258862 A1 Sep. 8, 2016

(30) Foreign Application Priority Data
Mar. 2, 2015 (KR) .......................... 10-2015-0029375

(51) Int. Cl.
*G01N 19/04* (2006.01)
*G01M 1/00* (2006.01)

(52) U.S. Cl.
CPC .............. *G01N 19/04* (2013.01); *G01M 1/00* (2013.01); *G01N 2203/0017* (2013.01); *G01N 2203/0025* (2013.01)

(58) Field of Classification Search
CPC ........... G01N 19/04; G01N 2203/0017; G01N 2203/0025; G01M 1/00
See application file for complete search history.

(56) References Cited

U.S. PATENT DOCUMENTS

| 6,117,695 A | 9/2000 | Murphy et al. |
| 6,513,374 B2 | 2/2003 | Goh et al. |
| 2004/0050152 A1 | 3/2004 | King |
| 2010/0206062 A1* | 8/2010 | Yoon ...................... G01N 19/04 73/150 A |

FOREIGN PATENT DOCUMENTS

EP 0582437 A2 * 2/1994 ............... G01N 3/00

* cited by examiner

*Primary Examiner* — Hezron E Williams
*Assistant Examiner* — David Z Huang

(57) ABSTRACT

A method includes providing a device under test, which includes a lower test layer and an upper test layer that is stacked on the lower test layer and includes an overhang protruding past an edge of the lower test layer by a predetermined length, fixing the lower test layer onto a mounting stage, and measuring adhesive force of an interlayer adhesive layer in a tensile mode by applying a load to a bottom surface of the overhang of the upper test layer in a first direction. An apparatus includes a mounting stage fixing the device under test, a load applying tip applying the load to the bottom surface of the overhang, a location adjuster adjusting a distance between the device under test and the load carrying tip, a load cell detecting a magnitude of the applied load, and a controller controlling the location adjuster and the load cell.

18 Claims, 13 Drawing Sheets

METHOD OF MEASURING AN ADHESIVE FORCE OF INTERLAYER ADHESIVE LAYER IN TENSILE MODE FOR STACKED SEMICONDUCTOR DEVICE AND APPARATUS FOR MEASURING THE SAME

CROSS-REFERENCE TO RELATED APPLICATION

This application claims the benefit of Korean Patent Application No. 10-2015-0029375, filed on Mar. 2, 2015, entitled "method of quantifying adhesive force of an interlayer adhesive layer in tensile mode for a stacked semiconductor device and a measurement apparatus for quantifying the same," which is hereby incorporated by reference in its entirety into this application.

BACKGROUND

Semiconductor chips (or dies) are packaged and electrically connected to an external circuit to constitute an electronic device. When a semiconductor chip is packaged, the semiconductor chip is attached onto another semiconductor chip or a substrate, such as a printed circuit board (PCB), via interlayer adhesive layer, such as adhesive paste or adhesive film.

In a semiconductor package including the interlayer adhesive layer, if adhesion strength of the interlayer adhesive layer is insufficient, a crack or an exfoliation may occur at the bonding interface between adjacent layers during fabrication or usage of the semiconductor package, thereby causing a defect in electric connections between semiconductor chips or between a semiconductor and a substrate, and, in some cases, causing a fracture in the stacked structure of the semiconductor package. Recently, as semiconductor devices become miniaturized, a thickness of an interlayer adhesive layer as well as that of a semiconductor package are significantly reduced, and thus the interlayer adhesive layer may be more susceptible to an occurrence of cracks or exfoliations of bonding interfaces. However, regardless of the reduced thickness of the interlayer adhesive layer, a reliability of the semiconductor package is more tightly required, and thus it is necessary for the adhesive layer to have sufficiently reliable adhesive force. Therefore, a quantitative method of measuring adhesive force is desirable as a method of evaluating reliability of a semiconductor package.

MIL-812 is a standard for quantitative measurement. The MIL-812 is limited to measurement of adhesive force in the shear mode with respect to a device under test (DUT). During packaging process, interlayer exfoliation associated with the interlayer adhesive layer may be caused not only by shear stress, but also tensile stress. Therefore, in measurements based on MIL-812, causes of defects in interlayer adhesive layer of a semiconductor package may not be precisely detected.

To measure adhesive force of interlayer adhesive layer in the tensile mode, it is necessary to apply tensile force to interface of the interlayer adhesive layer. To this end, a jig for applying a load may be fixed to any one of stacked semiconductor chips, which are combined with each other such that interlayer adhesive layer is disposed between adjacent chips. Then, the jig fixed to a corresponding semiconductor chip may be pulled. However, it is difficult to firmly fix a jig onto a semiconductor chip having a small thickness or size. Furthermore, specific material properties of the interlayer adhesive layer, such as thickness or adhesive force, may be changed during fixation of the jig. Thus, precise and reliable measurement is difficult.

SUMMARY

The present disclosure provides a method of measuring an adhesive force in a tensile mode for evaluating adhesive force and reliability of an interlayer adhesive layer applied to stacked semiconductor elements without mechanically fixing a separate jig to the interlayer adhesive layer or one of the stacked semiconductor elements, where the method may be applied to a conventional established mass production process for directly evaluating adhesive force and reliability of the interlayer adhesive layer from a device under test derived from the mass production process.

The present disclosure also provides an apparatus for measuring an adhesive force of an interlayer adhesive layer for stacked semiconductor elements in a tensile mode having the above-stated advantages.

According to an embodiment, a method of measuring an adhesive force of an interlayer adhesive layer for stacked semiconductor elements comprises: providing a device under test that includes a lower test layer, an upper test layer stacked on the lower test layer and including an overhang that protrudes past an edge of the lower test layer by a predetermined length; and the interlayer adhesive layer disposed between the lower test layer and the upper test layer and bonded to the lower test layer and the upper test layer; fixing the lower test layer onto a mounting stage; and measuring the adhesive force of the interlayer adhesive layer in a tensile mode by applying a load to a bottom surface of the overhang of the upper test layer in a first direction.

Each of the lower test layer and the upper test layer is a device layer, a substrate, two or more stacked device layers, two or more stacked substrates, or a stacked structure including one or more device layers and one or more substrates. The device layer comprises a semiconductor chip, a semiconductor die, a wafer, an encapsulated package, or a combination thereof, and wherein the substrate comprises a wafer, a lead frame, a die paddle, an interposer, a printed circuit board, a flexible printed circuit board, a film-type wire, or a combination thereof.

The interlayer adhesive layer comprises an adhesive layer or an adhesive agent. The device under test is an intermediate structure from a fabrication process of a semiconductor package. The semiconductor package may comprise device layers of a same type or device layers of different types.

The step of providing the device under test may comprise performing any one of a rotation process, a translation process, a flip process, or combination thereof to a first test layer and a second test layer, such that one of the first test layer and second test layers corresponds to the upper test layer and the other of the first and the second test layer corresponds to the lower test layer. The bottom surface of the overhang of the upper test layer comprises a surface of a passivation layer or a reinforcement layer.

The device under test has a wedge structure such that a length of the lower test layer in a second direction is greater than a length of the overhang of the upper test layer in the second direction, the second direction being perpendicular to the first direction, in order to concentrate tensile stresses at two end portions of a line of intersection between the overhang of the upper test layer and the edge of the lower test layer. The load may be applied by a load applying tip, and the load applying tip comprises a protruding portion. The protruding portion may include a convexly curved surface that contacts the bottom surface of the overhang during the application of the load.

A contact interface between at least a portion of the convexly curved surface and the bottom surface of the overhang is a linear contact interface that extends in a second direction which corresponds to a lengthwise direction of the overhang. The load may be applied by a load applying tip, wherein the load applying tip comprises a support and a base that is mounted on the support, wherein the base contacts the bottom surface of the overhang, and the base is tilted according to a tilt of the overhang.

The base may be tilted around an axis of rotation in a third direction perpendicular to the first and second directions. The third direction may correspond to a propagation of a crack in the interlayer adhesive layer. The load applying tip further comprises, a tilt supporting portion disposed between the support and the base and separating the support and the base from each other, and a trench accommodating the tilt supporting portion and allowing the tilt supporting portion to rotate about the axis of rotation to tilt the base. The trench may be provided on either the support or the base.

A cross-section of the tilt supporting portion has an arc shape or a circular shape with a first curvature, and the cross-section is perpendicular to a third direction and the third direction is perpendicular to the first and second directions and corresponds to a widthwise direction of the overhang. The trench has a second curvature identical to the first curvature of the tilt supporting portion.

The adhesive force may be measured by calculating an energy release rate according to a crack propagation at a first bonding interface of the interlayer adhesive layer and the upper test layer, a second bonding interface of the interlayer adhesive layer and the lower test layer, or both. In an embodiment, the energy release rate is calculated at a crack initiation time or a crack arresting time. Furthermore, the adhesive force may be defined by an energy release rate at a first crack arresting time.

According to an embodiment, an apparatus measures an adhesive force of an interlayer adhesive layer for a stacked semiconductor device, wherein the stacked semiconductor device is a device under test comprising a lower test layer and an upper test layer stacked on the lower test layer. The upper test layer may comprise an overhang that protrudes past an edge of the lower test layer by a predetermined length. The lower test layer and the upper test layer may be bonded together by the interlayer adhesive layer. The apparatus comprises: a mounting stage fixing the device under test; a load applying tip applying a load to a bottom surface of the overhang in a first direction; a location adjuster adjusting a distance between the device under test and the load applying tip to apply the load to the bottom surface of the overhang; a load cell detecting a magnitude of the applied load; and a controller controlling the location adjuster and the load cell.

The interlayer adhesive layer comprises an adhesive layer or an adhesive agent. Furthermore, the bottom surface of the overhang of the upper test layer comprises a passivation layer or a reinforcement layer. In an embodiment, the device under test has a wedge structure such that a length of the lower test layer in a second direction is greater than a length of the overhang of the upper test layer in the second direction, in order to concentrate tensile stresses at two end portions of a line of intersection between the overhang of the upper test layer and the edge of the lower test layer.

The load applying tip may comprise a protruding portion. The protruding portion may include a convexly curved surface that contacts the bottom surface of the overhang during the application of the load. At least a portion of the convexly curved surface may contact the bottom surface of the overhang along a line extending in a second direction. The second direction may correspond to a lengthwise direction of the overhang. The load applying tip may comprise a support and a base that is mounted on the support. The base may contact the bottom surface of the overhang, and the base may be configured to be tilted according to a tilt of the overhang.

The base may be tilted around an axis of rotation in a third direction perpendicular to the first and second direction. The third direction may correspond to a propagation direction of a crack in the interlayer adhesive layer. In an example, the load applying tip comprises: a tilt supporting portion disposed between the support and the base and separating the support and the base from each other; and a trench accommodating the tilt supporting portion and allowing the tilt supporting portion to rotate about an axis of rotation to tilt the base. The trench may be provided on either the support or the base.

A cross-section of the tilt supporting portion has an arc shape or a circular shape with a first curvature. The cross-section may be perpendicular to a third direction. The third direction may be perpendicular to the first and second directions and correspond to a widthwise direction of the overhang. The trench may have a second curvature identical to the first curvature of the tilt supporting portion. The tilt supporting portion and the trench extend in a third direction. The third direction may be perpendicular to the first and second directions and corresponds to a widthwise direction of the overhang. The controller may calculate an energy release rate according to a crack propagation at a first bonding interface of the interlayer adhesive layer and the upper test layer, a second bonding interface of the interlayer adhesive layer and the lower test layer, or both.

BRIEF DESCRIPTION OF THE DRAWINGS

The above and other features and beneficial aspects of embodiments of the present disclosure will become more apparent by describing in detail exemplary embodiments thereof with reference to the attached drawings in which.

DETAILED DESCRIPTION

Figure 1A:
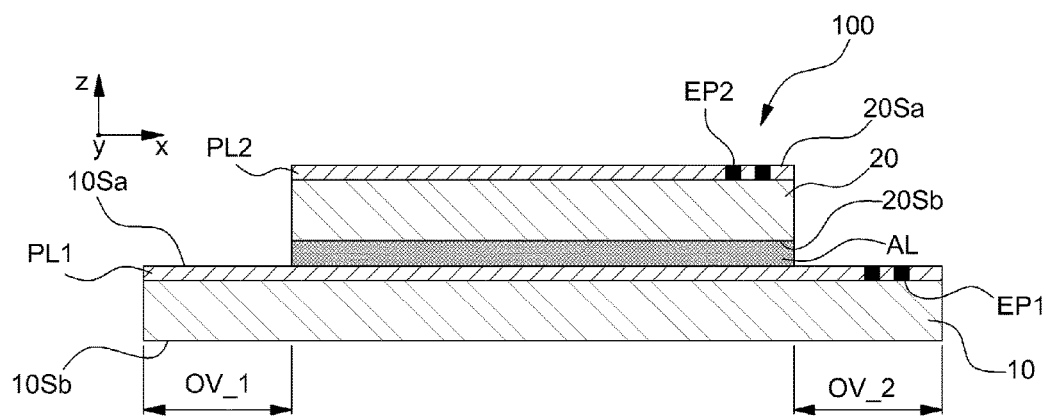
FIG. 1A is a diagram showing a device under test for measuring an adhesive force of an interlayer adhesive layer in a tensile mode.

Embodiments of the present disclosure will now be described more fully with reference to the accompanying drawings.

Embodiments of the present disclosure may, however, be embodied in many different forms and should not be construed as being limited to the embodiments set forth herein; rather, these embodiments are provided so that this disclosure will be thorough and complete, and will fully convey the concept of the present disclosure to one of ordinary skill in the art. Meanwhile, the terminology used herein is for the purpose of describing particular embodiments only and is not intended to be limiting of embodiments.

Also, thickness or sizes of layers in the drawings may be exaggerated for convenience of explanation and clarity, and the same reference numerals denote the same elements in the drawings. As used herein, the term "and/or" includes any and all combinations of one or more of the associated listed items.

The terminology used herein is for the purpose of describing particular embodiments only and is not intended to be limiting of exemplary embodiments. As used herein, the singular forms "a," "an" and "the" are intended to include the plural forms as well, unless the context clearly indicates otherwise. It will be further understood that the terms "comprises" and/or "comprising" used herein specify the presence of stated features, integers, steps, operations, members, components, and/or groups thereof, but do not preclude the presence or addition of one or more other features, integers, steps, operations, members, components, and/or groups thereof.

It will be understood that when a layer is referred to as being "formed on," another layer, it can be directly formed on the other layer or intervening layers may be present therebetween. Likewise, when a material is referred to as being adjacent to another material, intervening materials may be present therebetween. In contrast, when a layer or material is referred to as being "directly" formed on, to another layer or material or as being "directly" adjacent to or contacting another layer or material, there are no intervening materials or layers therebetween.

The relative terms including "below," "above," "upper," "lower," "horizontal," and "vertical" may be used to describe a relationship between an element, a layer, or a region and another element, another layer, or another region as shown in the drawings. It should be understood that the terms are not limited to the orientations shown in the drawings.

The term "device layer" used herein refers to, for example, any one of a semiconductor chip, a semiconductor die, a wafer, an encapsulated package, a stacked structure, and a combination thereof where electric circuits, such as, an analog circuit and/or digital circuit including transistor, memory cell, logic circuit, switch circuit, image pickup device, sensor, filter or RF circuit, are formed. Throughout the present disclosure, the term "substrate" refers to wafer, lead frame, die paddle, interposer, printed circuit board or flexible circuit board. Furthermore, the term "substrate" is not limited to the listed device layer, and it may be any structure having a surface on where the device layer can be stacked. For example, a flexible film type interconnection which is electrically insulated by a flexible polymer insulator layer may belong to the substrate, since the above device can be stacked on a surface of the flexible film type interconnection. In this disclosure, the term "test layer" may refer to the above device layer, a substrate, stacked substrates with two or more substrates, stacked device layers with two or more layers, or a stacked structure with at least one device layer and at least one substrate thereon. The stacked device layers and substrates are layers of a same type or different types. The stacked device layers and substrates also have the same shape or size, or different shapes or sizes.

Figure 1B:
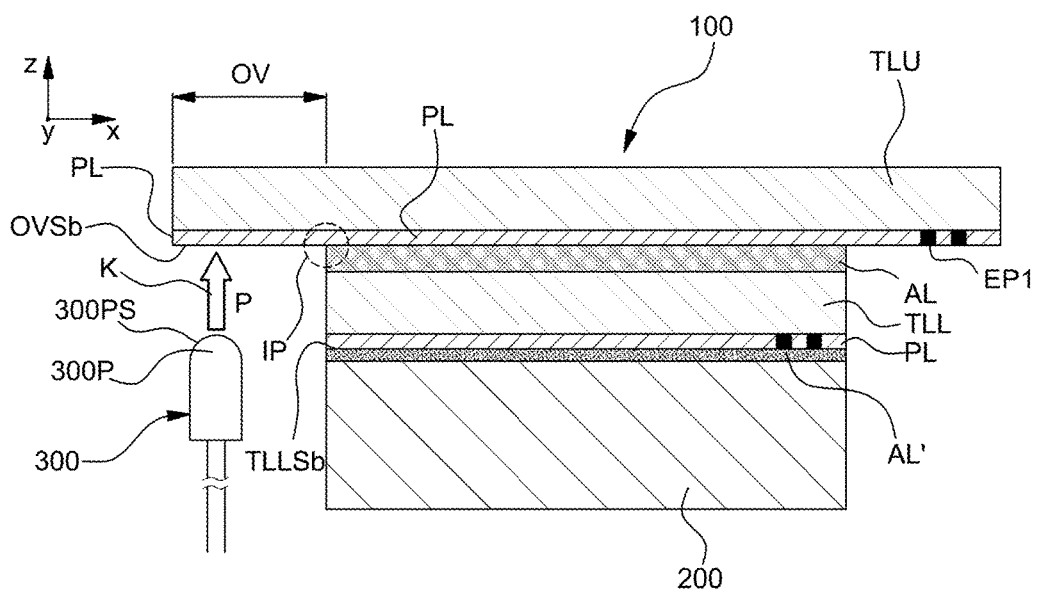
FIGS. 1B and 1C are cross-sectional view diagrams for describing a method of measuring the adhesive force of the interlayer adhesive layer in the tensile mode.
Figure 1C:
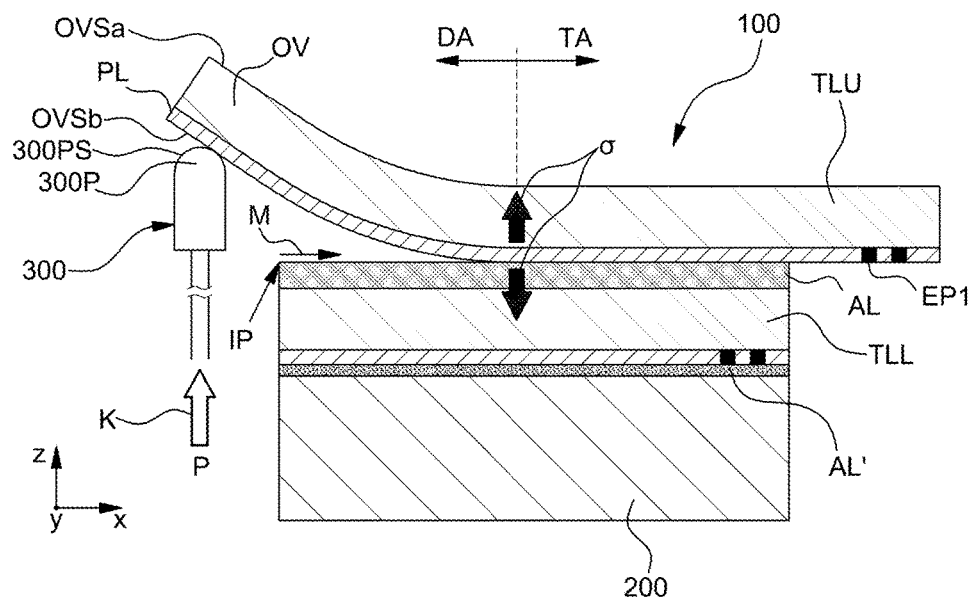

FIG. 1A is a diagram showing a device under test 100 for measuring adhesive force of an interlayer adhesive layer AL in a tensile mode, and FIGS. 1B and 1C are cross-sectional view diagrams for describing a method of measuring the adhesive force of the interlayer adhesive layer AL in the tensile mode.

Referring to FIG. 1A, the device under test 100 includes a stacked structure including a first test layer 10 and a second test layer 20. The first test layer 10 and the second test layer 20 are bonded with each other by the interlayer adhesive layer AL. The first test layer 10 and the second test layer 20 may be device layers of a same type, for example, for increasing capacity of a semiconductor device, or device layers of different types, for example, for implementing a system-in-package (SIP) for a composite semiconductor device. In an embodiment, one of the first test layer 10 and the second test layer 20 may be a semiconductor device, whereas the other of the first test layer 10 and the second test layer 20 may be a substrate. In another embodiment, at least one of the first test layer 10 and the second test layer 20 may have a stacked structure including two or more semiconductor devices, a stacked structure including two or more substrates, or a stacked structure including one or more semiconductor devices and one or more substrates.

If the first test layer 10 is a first semiconductor chip, a top surface 10Sa of the first test layer 10 may be an active surface in which an electronic circuit is disposed according to an embodiment. In an embodiment, the top surface 10Sa may be a surface of a first passivation layer PL1 illustrated in FIG. 1A, for example, an electrical insulation layer including silicon nitride, silicon oxide, or polymer. The first passivation layer PL1 is not limited to the electrical insulator, and the first passivation layer PL1 may be fabricated from magnetic shielding materials, thermal dissipation material, thermal screening material or other proper materials. A bottom surface 10Sb of the first test layer 10 may be a backside surface of the first semiconductor chip. Similarly, in an embodiment, if the second test layer 20 is a second semiconductor chip, a top surface 20Sa of the second test layer 20 may also be an active surface with a surface of a second passivation layer PL2 on the active surface, whereas a bottom surface 20Sb of the second test layer 20 may be a backside surface of the second semiconductor chip. In another embodiment (not shown), the top surface 20Sa of the second test layer 20 may be also a backside surface of a semiconductor chip, whereas the bottom surface 20Sb may be an active surface protected by a passivation layer.

The active surface of the semiconductor chip including the passivation layer may be more resistant to tensile stress than bare silicon surface. For example, if the passivation layer contains polymer, such as polyimide, polyethylene, or polypropylene, the active surface is more resistant to the tensile stress than the bare silicon surface corresponding to the bottom surface of the semiconductor chip. Therefore, as will be described below, a surface of a test layer on which a large tensile strain occurs during measurement of adhesive force of the interlayer adhesive layer AL in a tensile mode, for example, a surface contacted by a load applying tip, may be the active surface of a semiconductor with the passivation layer formed thereon.

The interlayer adhesive layer AL may include at least one adhesive film (e.g., die attach film), at least one adhesive paste (e.g., epoxy-based adhesive paste, silicone-based adhesive paste, or the like) or combination thereof. In an embodiment, the interlayer adhesive layer AL may be a die attach film suitable for use in an ultra-thin semiconductor package. The interlayer adhesive layer AL is not limited to electric insulators and may include conductive material and/or wirings for electric connection between the first test layer 10 and the second test layer 20. Furthermore, the interlayer adhesive layer AL may expand throughout a region where the first test layer 10 overlaps with the second test layer 20. The interlayer adhesive layer AL may have one or more through-holes arranged in a pattern for electrical connection or to pass a thermal flow, e.g., a cooling flow. Thus, the interlayer adhesive layer AL may partially expand such that the overlapped region between the first test layer 10 and the second test layer 20 are not entirely covered by the interlayer adhesive layer AL.

According to an embodiment, the device under test 100 may be an intermediate structure during a process of fabricating semiconductor package. For example, the intermediate structure may be a structure before a wire bonding process to electrically connect the first test layer 10 to the second test layer 20. In the embodiment shown in FIG. 1A, electrode pads EP1 and EP2 may be disposed at end portions of the first test layer 10 and the second test layer 20, respectively.

According to an embodiment, a width of the first test layer 10 may be different from that of the second test layer 20. FIG. 1A shows an embodiment in which the width of the first test layer 10 in the x-axis direction is greater than that of the second test layer 20 in the x-axis direction. The first test layer 10 may have portions that protrude past corresponding edges of the second test layer 20, and thus provide protruding portions OV_1 and OV_2. The device under test 100 including the protruding portions OV_1 and OV_2 may be an intermediate structure obtained during fabrication of a stacked semiconductor device. Detailed descriptions of various stacked semiconductor devices will be given below with reference to FIGS. 8A to 8D.

In the device under test 100 including the protruding portions OV_1 and OV_2 as an intermediate structure, first electrode pads EP1 for wire bonding may be disposed on a top surface of the protruding portion OV_1 or OV_2. Similarly, second electrode pads EP2 may be disposed on the second test layer 20. The electrode pads EP1 and EP2 may be electrically connected to each other, or each of the electrode pads EP1 and EP2 may be electrically connected to other chips and/or substrates via the wire bonding (e.g., using conductive wire WB as shown in FIGS. 8A to 8D).

The device under test 100 including the protruding portions OV_1 and OV_2 is not limited to an intermediate structure obtained from production of a stacked semiconductor device. The device under test 100 may be a device that is deliberately fabricated for the purpose of testing, or may be a device that is sampled from a production run. The device under test 100 may be a test vehicle for measurement of adhesive force of the interlayer adhesive layer AL in the tensile mode. As a test vehicle, the device under test 100 may be prepared such that one of the first test layer 10 and the second test layer 20 has one or more protruding portions. The device under test 100 with the protruding portions OV1 and OV2 for measurement of adhesive force in the tensile mode may be fabricated by rotating, translating, or flipping the first test layer 10 and the second test layer 20 with respect to each other, regardless of whether the first test layer 10 and the second test layer 20 have a same size and a same shape. Detailed descriptions thereof will be given below with reference to FIGS. 3A to 3C.

FIG. 1A shows that the first test layer 10 extends in the x-axis direction past two opposite edges of the second test layer 20 and includes the protruding portions OV_1 and OV_2. However, embodiments of the present disclosure are not limited thereto. For example, the protruding portions OV_1 and OV_2 may extend in a first direction (e.g., the x-axis direction shown in FIG. 1A) past only a first corresponding edge of the second test layer 20 and/or extend in a second direction (e.g., the y-axis direction perpendicular to the x-axis direction shown in FIG. 1A) past only a second corresponding edge of the second test layer 20. The protruding portions (not shown) may expand in two directions (e.g., the x-axis and y-axis directions) parallel to the top surface 20Sa of the second test layer 20 such that the protruding portions extend past three or four edges of the second test layer 20. In other words, in various embodiments, one or more protruding portion may extend in one or more direction to overhang over the second test layer 20. Furthermore, although not shown, the second test layer 20 may also extend in the x-direction past the edges of the first test layer 10 such that the second test layer 20 may have protruding portions.

Referring to FIG. 1B, in order to measure an adhesive force of the interlayer adhesive layer AL, the device under test 100 of FIG. 1A may be turned upside down, such that the first test layer 10 of FIG. 1A including the protruding portions OV_1 and OV_2 becomes an upper test layer TLU of FIG. 1B. Therefore, one of the protruding portions OV_1 and OV_2 of the first test layer 10 corresponds to an overhang OV that extends past an edge of a lower test layer TLL. In the present disclosure, the overhang OV refers to a protruding portion that a load applying tip 300 contacts and applies a load P thereto for measuring an adhesive force of the interlayer adhesive layer AL in a tensile mode.

Hereinafter, as shown in FIG. 1B, a layer corresponding to the first test layer 10 of FIG. 1A, which is provided as the top layer of the device under test 100 and includes the overhang OV during measurement of adhesive force in a tensile mode will be referred to as the upper test layer TLU, whereas a layer corresponding to the second test layer 20 of FIG. 1A, which is disposed below the upper test layer TLU, will be referred to as a lower test layer TLL.

In order to measure an adhesive force of the interlayer adhesive layer AL in the tensile mode, the bottom surface TLLSb of the lower test layer TLL of the device under test 100, which corresponds to the top surface 20Sa of the second test layer 20 of FIG. 1A, may be fixed on a mounting element. The mounting element may be a mounting stage 200, which may comprise a metal block or a table. The mounting stage 200 may mechanically fix the device under test 100. In an embodiment, the device under test 100 may be fixed onto the mounting stage 200 by disposing a fixing adhesive element (or a fixing adhesive layer) AL' between the bottom surface TLLSb of the lower test layer TLL and a top surface of the mounting stage 200. The fixing adhesive element AL' may include a firm and strong adhesive material that exhibits greater adhesive force in a tensile mode and in a shear mode than the interlayer adhesive layer AL. A deformation of the fixing adhesive element AL' is small enough during measurement of adhesive force in the tensile mode not to affect compliance of the upper test layer TLU. In an embodiment, the fixing adhesive element AL' may be an epoxy-based adhesive or a double-sided tape.

Referring to FIG. 1C with FIG. 1B, as indicated by the arrow K, a load P is applied to the bottom surface OVSb of the overhang OV of the upper test layer TLU by moving the load applying tip 300 in a third direction (e.g., the z-axis direction). The load applying tip 300 moving in the z-axis direction contacts the bottom surface OVSb of the overhang OV and applies the load P in a substantially perpendicular direction to the bottom surface OVSb of the overhang OV. As the overhang OV of the upper test layer TLU is pushed upward by the load P, a tensile stress σ is applied to the interlayer adhesive layer AL disposed between the upper test layer TLU and the lower test layer TLL as shown in FIG. 1C. The upper test layer TLU may experience deformation which is caused by bending of the overhang OV. Moreover, if the load P increases, a crack may be generated at the adhesion interface between the upper test layer TLU and the lower test layer TLL. The position where such a crack may be generated may vary according to material properties of the upper test layer TLU, the lower test layer TLL, and the interlayer adhesive layer AL, or according to adhesive force of the interlayer adhesive layer AL with respect to the upper test layer TLU and the lower test layer TLL. For example, as shown in FIG. 1C, a crack may be generated between the interlayer adhesive layer AL and the upper test layer TLU. In other embodiments, a crack may be generated between the interlayer adhesive layer AL and the lower test layer TLL or inside the interlayer adhesive layer AL. The term "crack" is used here to describe diverse failure modes from the tensile test, including failure of an adhesive bond between an adhesive element and a semiconductor element, and mechanical separation, or delamination, internal to the adhesive element.

The crack may propagate across the inner side of the adhesion interface from an edge portion IP of an overlapped region between the upper test layer TLU and the lower test layer TLL, as indicated by the arrow M. The crack may propagate across the inner side of the adhesion interface from an edge portion IP of an overlapped region between the upper test layer TLU and the lower test layer TLL via the interlayer adhesive layer A1, as indicated by the arrow M. The edge portion IP of the overlapped region may be a portion of the overlapped region between the upper test layer TLU and the lower test layer TLL, and the edge portion may be adjacent to the overhang OV. The crack may propagate in the x-axis direction perpendicular to the z-axis direction in which the load P is applied, in the orthogonal coordinate system shown in FIG. 1C. Hereafter in the present disclosure, the x-axis direction (or the first direction) may also be referred to as a lengthwise direction of the overhang OV (or a lengthwise direction the upper test layer TLU), whereas the y-axis direction (or the second direction) may be also referred to as a widthwise direction of the overhang OV (or a widthwise direction of the upper test layer TLU). In an embodiment, a length of the overhang OV in the lengthwise direction is greater than a length of the overhang OV in the widthwise direction.

Reference characters DA and TA refer to a cracked region and a non-cracked region (that is, a bonded region) between the upper test layer TLU and the lower test layer TLL, respectively. The load P gradually decreases after a crack is initiated, and, as will be described below, adhesive force of the interlayer adhesive layer AL may be calculated by using an energy release rate Gc based on the crack propagation.

When the overhang OV is bent, a compression stress occurs on the top surface OVSa of the overhang OV, whereas a tensile stress occurs on the bottom surface OVSb of the overhang OV. Generally, a semiconductor chip is more vulnerable to a tensile stress than to a compression stress. Therefore, it may be desirable that the bottom surface OVSb of the overhang OV, to which the tensile stress is applied, is reinforced to become more resistant to tensile deformation. For example, the bottom surface of the overhang OV may be the active surface of a semiconductor chip reinforced by the passivation layer PL. To this end, the device under test 100 may be turned upside down as shown in FIG. 1B so that measurement of adhesive force in the tensile mode may be performed.

In an embodiment, an additional reinforcement layer like the passivation layer PL may be formed on the bottom surface OVSb of the overhang OV. In an embodiment, when the device under test 100 is a test vehicle. a reinforcement layer like the passivation layer PL may be deliberately formed on the bottom surface OVSb of the overhang OV such that the bottom surface OVSb of the overhang OV can be rendered to be more resistant to the tensile deformation. The reinforcement layer may include a polymer resin-based material, an oxide, or a nitride. The reinforcement layer may not be significantly deformed when the load applying tip 300 presses the reinforcement layer. Since adhesive force to the interlayer adhesive layer AL may vary according to a material of the reinforcement layer, a particular material may be selected as a reference for measuring adhesive force.

The load applying tip 300 is a movable component, such as a jig or a rod that may contact the bottom surface OVSb of the overhang OV of the upper test layer TLU. The load applying tip 300 applies a predetermined force on the bottom surface OVSb for application of the load P. The load applying tip 300 may maintain contact with the bottom surface OVSb while the load P is applied to the bottom surface OVSb of the overhang OV.

In an embodiment, as shown in FIGS. 1B and 1C, the load applying tip 300 may include a protruding portion 300P having a convexly curved surface 300PS contacting the bottom surface OVSb of the overhang OV. The protruding portion 300P may extend in the widthwise direction, or y-axis direction, of the overhang OV to cause a line-contact between the protruding portion 300P and the bottom surface OVSb of the overhang OV. In another embodiment, the protruding portion 300P may be designed to cause a surface-contact between the protruding portion 300P and the bottom surface OVSb of the overhang OV, rather than the line-contact. In other words, a tensile load may be applied to bottom surface OVSb through a point of contact, a linear contact surface, or a two dimensional contact surface. Preferably, in an embodiment, a contact interface between the protruding portion 300P and the bottom surface of the overhang OVSb is a linear contact interface that extends a second direction (y direction), which is a widthwise direction of the overhang.

While the overhang OV is bent by the load P, a contact region (e.g., a line-contact region) between the bottom surface OVSb of the overhang OV and the protruding portion 300P of the load applying tip 300, may be moved infinitesimally along the surface 300PS of the load applying tip 300 in the x-axis direction, thereby reducing or eliminating an effect to compliance of the bent overhang OV.

Figure 2:
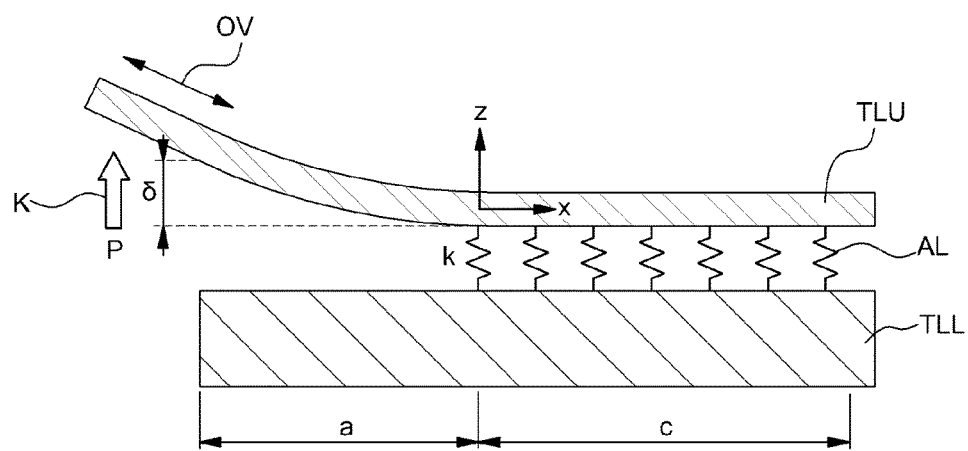
FIG. 2 is a cross-sectional view diagram for describing a relationship between an applied load and adhesive force of the interlayer adhesive layer, according to an embodiment of the present disclosure.

FIG. 2 is a cross-sectional view diagram for describing a relationship between an applied load P and adhesive force of an interlayer adhesive layer AL, according to an embodiment of the present disclosure.

Referring to FIG. 2, deformation of an upper test layer TLU including an overhang OV when the load applying tip 300 of FIG. 1C, which applies the load P in the z-axis direction vertically and moves by a distance b, may be described based on the Euler-Bernoulli Beam theory or the Winkler foundation model. In FIG. 2, reference characters a, c, and k denote a crack length, an uncracked ligament length, and a foundation modulus, respectively. In this embodiment shown in FIG. 2, an energy release rate Gc may be calculated from the deformation of the upper test layer TLU according to Equation 1.

$$G_C = \frac{P_c^2}{2b} \frac{dC}{da}$$ [Equation 1]

In Equation 1, $P_c$ denotes a critical load, a denotes the crack length, b denotes a length of the overhang OV in a direction perpendicular to the x and z directions of FIG. 2, and C denotes a compliance of the upper test layer TLU. The compliance may be obtained according to Equation 2.

$$C = \frac{4\lambda}{\kappa}\left[\frac{\lambda^3 a^3}{3} + \lambda^2 a^2 + \lambda a + \frac{1}{2}\right]$$ [Equation 2]

In Equation 2, a wave number $\lambda$ and the foundation modulus k may be obtained according to Equations 3 and 4, respectively.

$$\lambda = \left[\frac{3\kappa}{E_s t_s^3 b}\right]^{\frac{1}{4}}$$ [Equation 3]

$$\kappa = \frac{(1-v_f)}{(1-2v_f)(1+v_f)} \frac{E_f b}{t_f}$$ [Equation 4]

In Equation 4, E and v respectively denote an elastic modulus and a Poisson's ratio, and t denotes a thickness. The subscripts s and f denote the upper test layer TLU functioning as a cantilever beam and the interlayer adhesive layer AL, respectively. According to the above equations, the energy release rate of Equation 1 may be expressed as shown in Equation 5 below.

$$G_C = \frac{P_c^2}{2b} \frac{4\lambda}{\kappa}[\lambda^3 a^2 + 2\lambda^2 a + \lambda].$$ [Equation 5]

According to Equation 5, an energy release rate Gc according to a crack propagation may be determined and adhesive force of the interlayer adhesive layer AL in the tensile mode may be obtained. The unit of the energy release rate Gc is J/mm$^2$, and the energy release rate Gc indicates adhesive force of the interlayer adhesive layer AL.

Figure 3A:
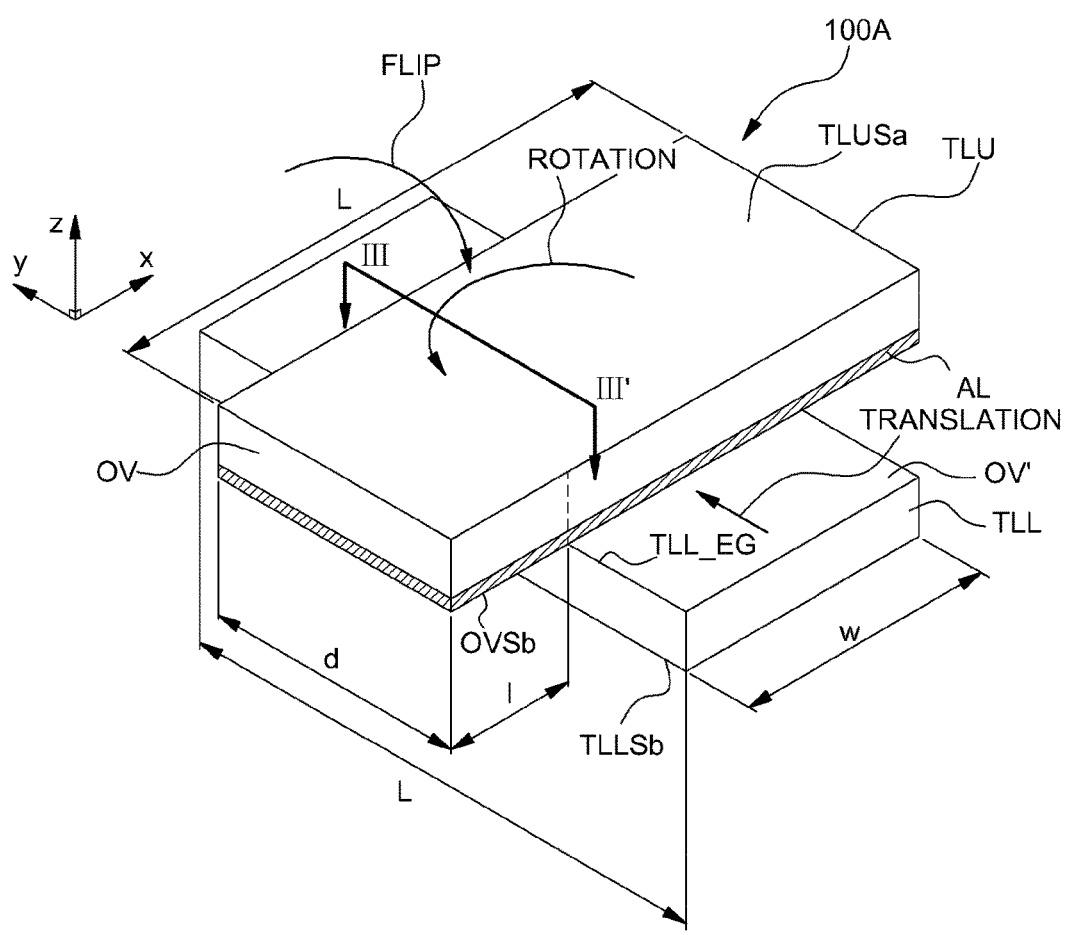
FIGS. 3A and 3B are perspective view diagrams showing methods of preparing device under tests and according to various embodiments of the present disclosure.
Figure 3B:
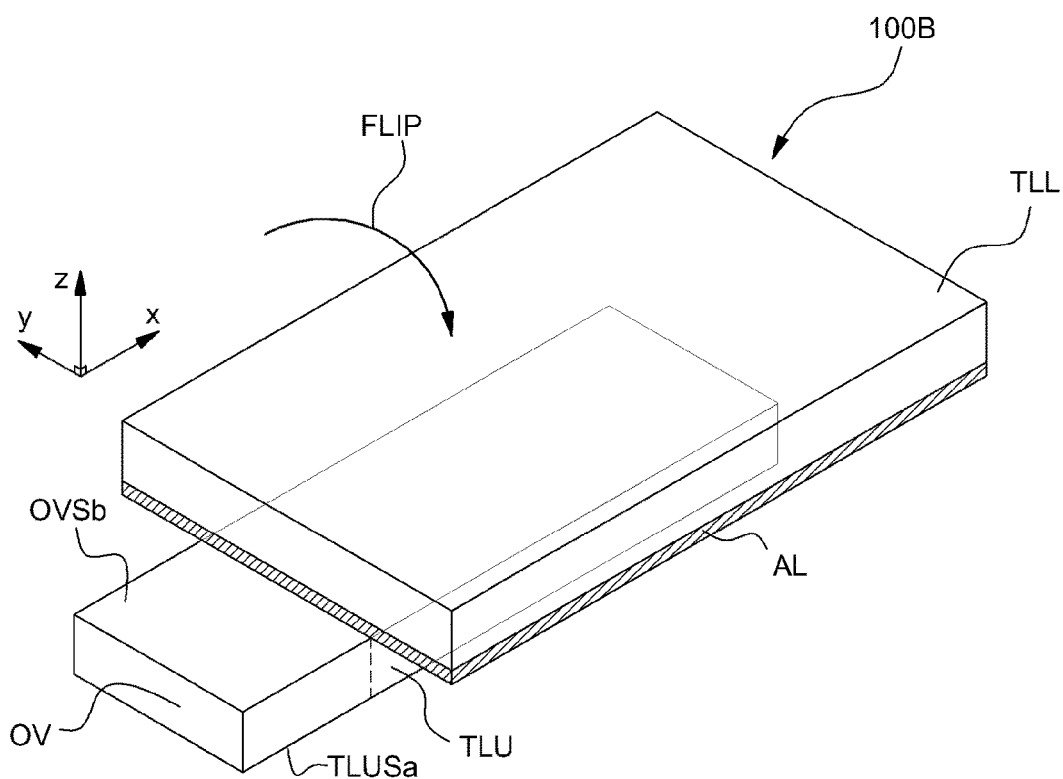

FIGS. 3A and 3B are perspective view diagrams showing methods of providing device under tests 100A and 100B according to various embodiments of the present disclosure.

Referring to FIG. 3A, in order to provide the device under test 100A having a first overhang OV according to an embodiment, a rotation process, a translation process, or a flip process may be performed on a first test layer and a second test layer. For example, the first test layer and the second test layer, which may have a same width, a same length, and a same shape (e.g., a rectangular parallelepiped shape), are vertically stacked, may be rotated by a certain angle, e.g., 90°, or linearly translated by a certain distance with respect to each other, and then flipped such that one of the first test layer and the second test layer may correspond to the upper test layer TLU that provides the first overhang OV of the device under test 100A. In other words, in some embodiments, the orientation of various layers of a stacked semiconductor device may be adapted relative to a nominal orientation of a production device to provide one or more overhang OV. The first overhang OV may have a length l in the x-axis direction (or the lengthwise direction of the first overhang OV) parallel to a direction in which a crack propagates as a load P is applied, and a length d in the y-axis direction (or the widthwise direction of the first overhang OV) perpendicular to the x-axis direction.

In an embodiment, a layer that was originally arranged below the other layer may be arranged above the other layer by turning the vertical stack of the first test layer and the second test layer upside down, or flipping the stack, thereby providing the overhang unit OV of the device under test 100A. In an embodiment, the bottom surface OVSb of the overhang OV may include a passivation layer or a reinforcement layer that is resistant to tensile deformation and impact.

The rotation process, the translation process, or the flip process may be processes for fabricating a stacked semiconductor package. Therefore, the device under test 100A according to an embodiment of the present disclosure may be an intermediate structure prior to a final product.

By performing the above-described processes on the first test layer and the second test layer, as shown in FIG. 3A, the upper test layer TLU is disposed on the lower test layer TLL to have the overhang OV. Surfaces of the upper test layer TLU and the lower test layer TLL that face each other are bonded together by using the interlayer adhesive layer AL to determine adhesive force of the interlayer adhesive layer AL, thereby providing the device under test 100A that has the overhang OV. Next, the adhesive force of the interlayer adhesive layer AL may be determined by applying a load to the bottom surface OVSb of the overhang OV in the z-axis direction, that is, a vertically upward direction. To this end, for example, the bottom surface TLLSb of the lower test layer TLL may be fixed to the mounting stage 200 of FIG. 1A and the load may be applied to the bottom surface OVSb of the overhang OV of the upper test layer TLU, and, then, adhesive force of the interlayer adhesive layer AL may be determined.

According to another embodiment, in order to determine the adhesive force of the interlayer adhesive layer AL by applying a load to a second overhang OV' of the lower test layer TLL, the device under test 100A shown in FIG. 3A may be turned upside down. In this case, the top surface TLUSa of the upper test layer TLU of the device under test 100A may be fixed onto the mounting stage. Then, the load may be applied to the bottom surface of the second overhang OV' of the lower test layer TLL to measure the adhesive force of the interlayer adhesive layer AL in the tensile mode.

Referring to FIG. 3B, a device under test 100B may include test layers, which are combined with each other via an interlayer adhesive layer AL and have different sizes and shapes. For example, the device under test 100B may be a stacked structure consisting of device layers of different types or a stacked structure consisting of a device layer and a substrate. FIG. 3B shows the device under test 100B before the device under test 100B is turned upside down to apply a load to determine adhesive force of the interlayer adhesive layer AL. Therefore, when the device under test 100B is flipped as indicated by an arrow FLIP, the bottom layer of the stacked structure becomes an upper test layer TLU, and a protruding portion of the upper test layer TLU corresponds to an overhang OV suitable for evaluation of adhesive force in a tensile mode. In this case, a load applying tip will contact the bottom surface OVSb of the overhang OV and the adhesive force of the interlayer adhesive layer AL in the tensile mode will be measured.

If test layers of a device under test have different sizes and shapes as shown in FIG. 3B, degree of freedom for performing processes, such as a rotation process, a translation process, a flip process, or a combination thereof to prepare the overhang OV may increase. As a result, a stacked structure of the device under test 100B and shapes and sizes of the overhang OV for measuring an adhesive force of the interlayer adhesive layer AL may be provided in a diverse a of configurations.

Figure 4A:
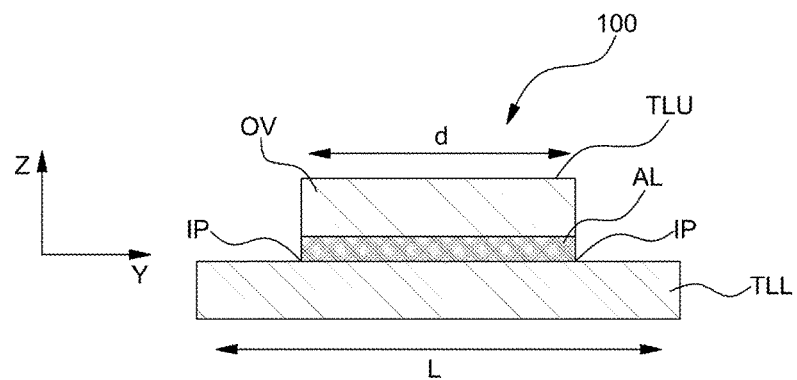
FIG. 4A is a cross-sectional view diagram of a device under test according to an embodiment.
Figure 4B:
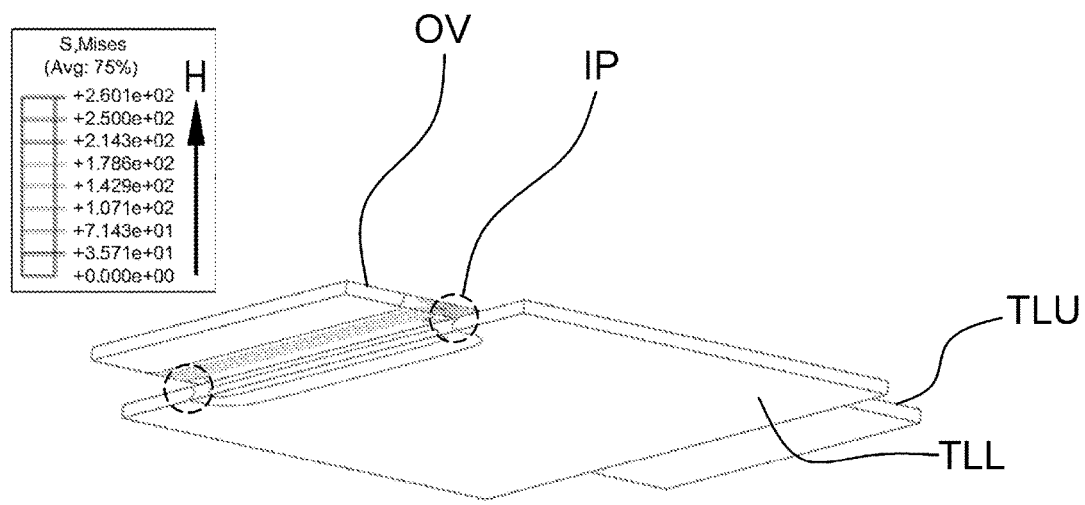
FIG. 4B is a diagram showing a distribution of stresses in the device under test of FIG. 4A based on a finite element simulation.

FIG. 4A is a cross-sectional view diagram of a device under test 100 according to an embodiment, and FIG. 4B is a diagram showing a stress distribution of the device under test 100 of FIG. 4A based on a finite element simulation.

Referring to FIG. 4A, the cross-sectional view of the device under test 100 is shown along a line III-III' parallel to the y-axis direction (e.g., the widthwise direction of the overhang OV of FIG. 3A). The line III-III' is a line parallel to a line of intersection between the overhang OV of the upper test layer TLU and an edge TLL_EG of FIG. 3A of the lower test layer TLL. The device under test 100 may have a wedge structure in which a base layer is wider than a top layer shown in FIG. 4A, so that an initial interlayer crack may easily occur when a load is applied to the bottom surface of the overhang OV of the upper test layer TLU.

In the wedge structure, a length L of the edge TLL_EG of the lower test layer TLL is greater than a length d of the overhang OV of the upper test layer TLU. An example of the wedge structure is illustrated in FIG. 4B. Generally, if adhesive force of the interlayer adhesive layer AL is high, it is difficult to cause the upper test layer TLU or the lower test layer TLL to separate from the interlayer adhesive layer AL. Therefore, in order to facilitate measuring adhesive force of the interlayer adhesive layer AL, it may be desirable to make an initial crack easily occur at an interface region between the upper test layer TLU and the lower test layer TLL.

The wedge structure can concentrate stresses at two end portions IP of the wedge structure, where the two end portions IP corresponds to both end portions of a line of intersection between a bottom surface of the overhang OV of the upper test layer TLU and the edge TLL_EG of the lower test layer TLL. The concentration of stress facilitates formation of an initial crack of the interlayer adhesive layer AL, and thus it becomes easy to measure adhesive force of the interlayer adhesive layer AL according to a propagation of the crack.

Referring to FIG. 4B, the stress distribution proximate to the line of intersection between the bottom surface of the overhang OV of the upper test layer TLU and the edge TLL_EG of the lower test layer TLL is shown. A magnitude of the stress increases in a direction indicated by the arrow H. Here, as the closer to the two end portions IP, the stress lines become the denser. Due to the higher stresses concentrated at the two end portions IP of the wedge structure, cracks may be easily generated at the two end portions IP. Therefore, the wedge structure easily induces initial cracks of the device under test 100, and thus adhesive force of the interlayer adhesive layer AL may be easily measured.

Figure 5A:
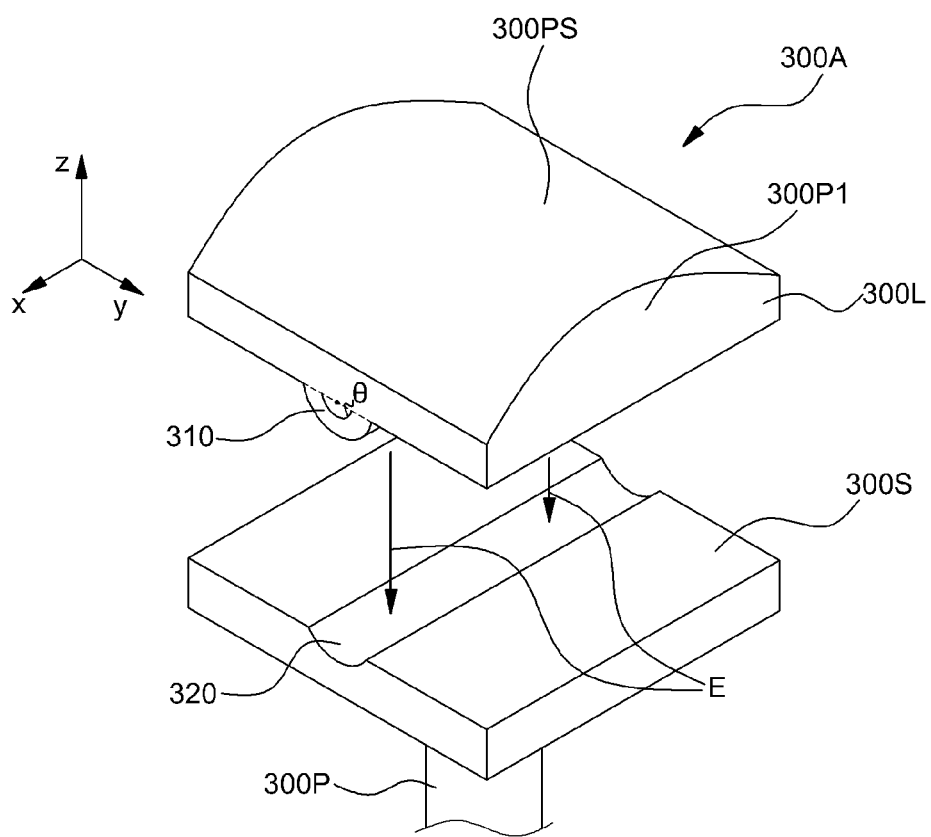
FIG. 5A is an exploded perspective view of a load applying tip according to an embodiment of the present disclosure.
Figure 5B:
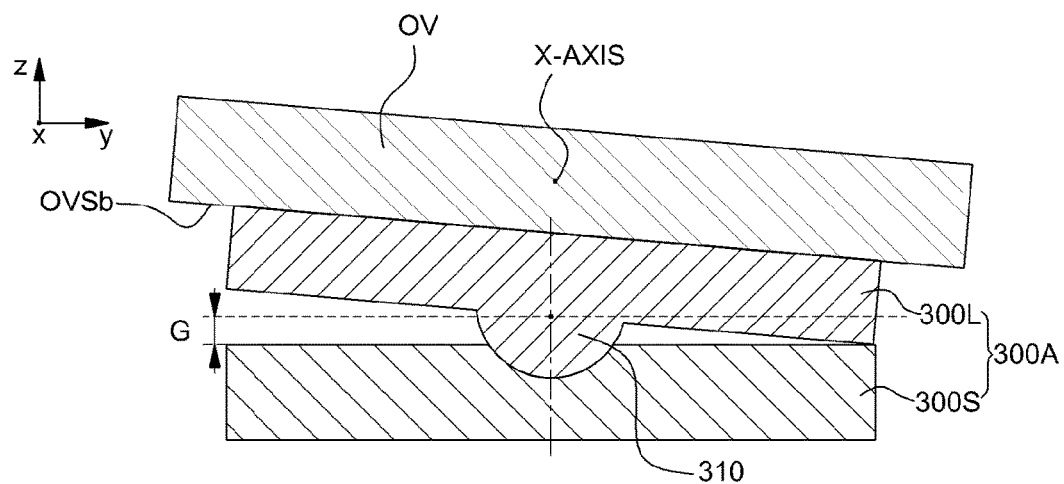
FIG. 5B is a cross-sectional view of an operation mechanism of the load applying tip of FIG. 5A.
Figure 5C:
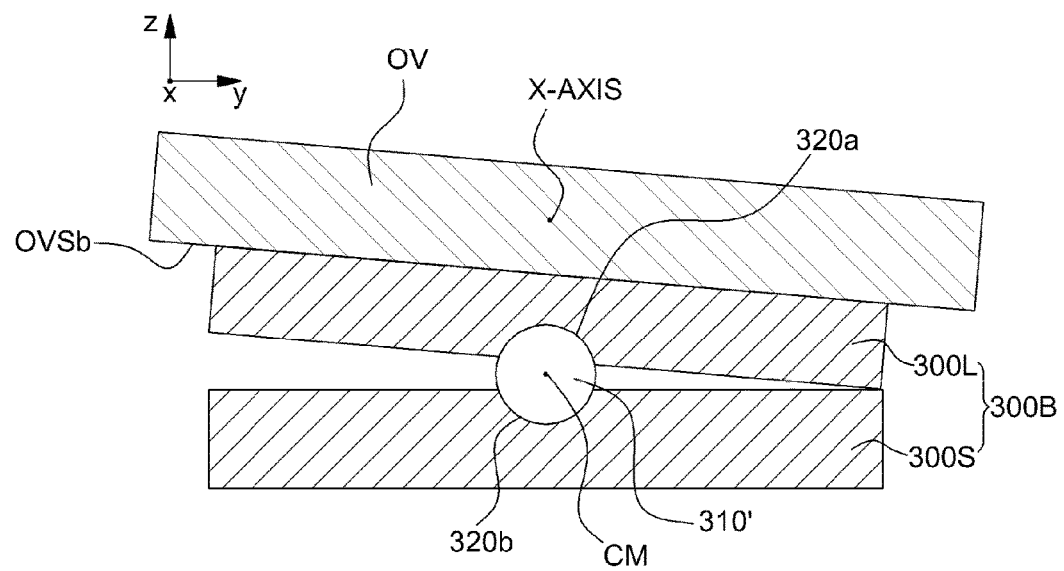
FIG. 5C is a cross-sectional view diagram of a load applying tip according to another embodiment of the present disclosure.

FIG. 5A is an exploded perspective view of a load applying tip 300A according to an embodiment, FIG. 5B is a cross-sectional view of an operation mechanism of the load applying tip 300A of FIG. 5A, and FIG. 5C is a cross-sectional view diagram of a load applying tip 300B according to another embodiment.

Referring to FIGS. 5A and 5B, the load applying tip 300A includes a supporting element (or a support) 300S and a base element (or a base) 300L. The base element 300L is mounted on the supporting element 300S and separated from the supporting element 300S such that the base element 300L can be tilted with respect to the supporting element 300S. The base element 300L contacts the bottom surface of the overhang OV to apply a vertically upward load to the overhang OV of an upper test layer. The reference number 300P refers to a connected portion or a clamped portion configured to transfer a force from an external power device (e.g., a motor) to the bottom surface of the overhang OV and to move the load applying tip 300A.

The load applying tip 300A may include a tilt supporting portion 310 provided between the supporting element 300S and the base element 300L. For example, the tilt supporting portion 310 may be a part of the supporting element 300S or the base element 300L. In an embodiment, the tilt supporting portion 310 may be provided on the bottom surface of the base element 300L as shown in FIG. 5A. In this embodiment, the tilt supporting portion 310 may be integrated with the bottom surface of the base element 300L.

At least a portion of a cross-section of the tilt supporting portion 310, where the cross-section is parallel to the z-y plane or perpendicular to a direction (e.g., the x-axis direction or the lengthwise direction of the overhang) in which crack of an interlayer adhesive layer propagates as a load P is applied, has an arc shape with a predetermined curvature, and the arc shape may extend in the x-axis direction. The tilt supporting portion 310 functions as a fulcrum of a lever formed by the supporting element 300S and the base element 300L, such that the base element 300L of the load applying tip 300A may be tilted like a see-saw. If the cross-section of the tilt supporting portion 310 has an arc shape, angle θ of the arc may be 180°, for example. However, it is merely an example, and the angle θ of the arc may be greater than 0° and smaller than or equal to 180°.

The supporting element 300S may further include a trench 320 that accommodates the tilt supporting portion 310 and allows the tilt supporting portion 310 to rotate about the x-axis, such that the base element 300L may be tilted. In an embodiment, the trench 320 may have substantially the same curvature as that of the arc of the tilt supporting portion 310. In this embodiment, the trench 320 may extend in the x-axis direction like the tilt supporting portion 310.

In an embodiment, as indicated by the arrow E, by placing the base element 300L on the supporting element 300S, the tilt supporting portion 310 of the base element 300L fits the trench 320 of the supporting element 300S, and thus the base element 300L may be combined with the supporting element 300S and configured to tilt about the x-axis as the center rotation axis. In an embodiment, the tilt supporting portion 310 and the trench 320 may pass through the center of mass of the base element 300L.

As shown in FIG. 1C, in order to apply a load P to the overhang OV precisely in a vertically upward direction (e.g., the z-axis direction) and accurately measure compliance of the upper test layer TLU, it is desirable to precisely align the device under test 100 when the device under test 100 is fixed onto the mounting element 200. While the device under test 100 is being fabricated or the device under test 100 is fixed onto the mounting stage 200, the device under test 10 may be occasionally tilted, and more particularly, the overhang OV may be tilted, and thus the device under test 100 may not be precisely aligned.

A tilt of the overhang OV about the y-axis or the z-axis may be substantially prevented from affecting a measured value of adhesive force by appropriately setting a measurement apparatus. However, due to a variation of a thickness of the interlayer adhesive layer AL, the overhang OV may be tilted about the x-axis. In this case, the tilt of the overhang OV about the x-axis renders a contact region between the load applying tip 300 and the bottom surface OVSb of the overhang OV non-uniform in the y-axis direction, thereby interrupting application of the load P to the overhang OV precisely in a vertically upward direction (e.g., the z-axis direction). Therefore, it is desirable to reduce or compensate for such a tilt of the overhang OV about the x-axis during measurement of adhesive force in a tensile mode.

As shown in FIG. 5B, if the overhang OV is tilted about the x-axis as the center rotation axis, the base element 300L of the load applying tip 300A according to an embodiment is tilted about the x-axis to compensate for the tilted angle of the overhang OV about the x-axis, thereby compensating for misalignment of the device under test 100 tilted about the x-axis. As a result, the load P may be applied to the overhang OV precisely in a direction orthogonal to an adhesive interface, which may be a vertically upward direction (e.g., the z-axis direction).

In an embodiment, for the base element 300L to be smoothly tilted, a height of the tilt supporting portion 310 may be greater than a depth of the trench 320 to provide a clearance G between a bottom surface of the base element 300L and a top surface of the supporting element 300S. The clearance G may be in a range from about 50 μm to about 700 μm, for example.

Although not shown, according to another embodiment, unlike the structure shown in FIG. 5A, a trench having a first arc portion may be formed on the bottom surface of the base element 300L, and a tilt supporting portion having a second arc portion to fit the trench may be provided on the top surface of the supporting element 300S. In this embodiment, the tilt supporting portion may be integrated with the top surface of the supporting element 300S.

Referring to FIG. 5C, a cross-section of a tilt supporting portion 310' of a load applying tip 300B according to an embodiment is parallel to the z-y plane and perpendicular to a direction (e.g., the x-axis direction or the lengthwise direction of the overhang) in which a crack of an interlayer adhesive layer propagates as a load P is applied and may have an arc shape with a predetermined curvature. In this embodiment, the tilt supporting portion 310' may be a cylinder having a center axis CM extending in the x-axis direction and the cylinder has a predetermined radius. In this embodiment, trench portions 320a and 320b, which accommodate the tilt supporting portion 310' and allow the tilt supporting portion 310' to move with respect to the bottom surface of the base element 300L and the top surface of the supporting element 300S, may be formed on the bottom surface of the base element 300L and the top surface of the supporting element 300S, respectively. Curvatures of the trenches 320a and 320b may be substantially identical to that of the tilt supporting portion 310'.

In the embodiments described above with reference to FIGS. 5A to 5C, a lubrication interface for reducing or substantially eliminating friction between the tilt supporting portion 310 or 310' and the trench 320, 320a, or 320b may be provided on an interface between the tilt supporting portion 310 or 310' and the trench 320, 320a, or 320b. In an embodiment, bearings may be further provided on at least one of the supporting element 300S and the base element 300L.

The base element 300L may include a protruding portion 300P1 that has a convexly curved surface 300PS. In order to provide the protruding portion 300P1, the entire top surface of the base element 300L may be the convexly curved surface 300PS. FIG. 5A shows the protruding portion 300P1 that is a semi-cylinder. The convexly curved surface 300PS of the protruding portion 300P1 may ensure a linear contact interface between the load applying tip 300A and the overhang OV, where the linear interface extends in the y-axis direction.

In an embodiment, at least a portion of the protruding portion 300P1 may have a curved surface with a predetermined curvature. In an embodiment, while the overhang OV is bent, the protruding portion 300P1 may reduce or eliminate effects on the compliance of the bent overhang OV, because the contact region between the bottom surface OVSb of the overhang OV and the protruding portion 300P1 of the load applying tip 300, that is, a straight line extending in the y-axis direction infinitesimally moves along the surface 300PS.

Figure 6:
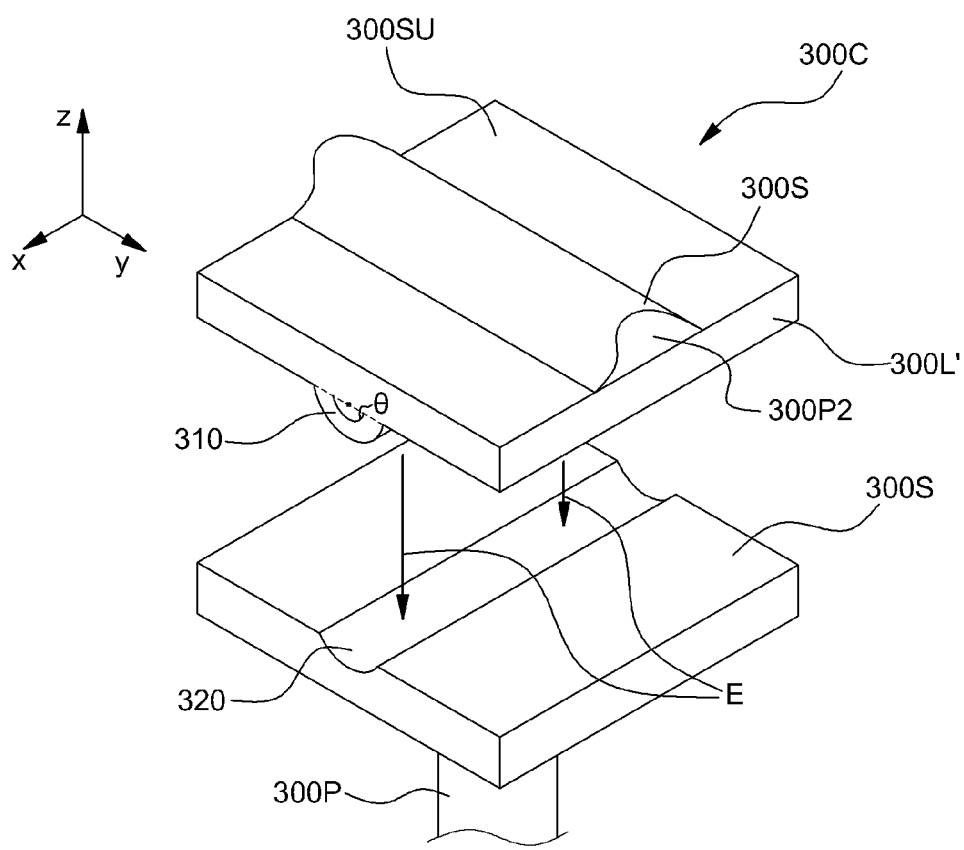
FIG. 6 is an exploded perspective view of a load applying tip according to another embodiment of the present disclosure.

FIG. 6 is an exploded perspective view of a load applying tip 300C according to another embodiment of the present disclosure.

Referring to FIG. 6, the load applying tip 300C includes a supporting element 300S and a base element 300L' that is tiltably mounted on the supporting element 300S. The load applying tip 300C includes the tilt supporting portion 310 and the trench 320 such that the base element 300L' is tilted to compensate for a tilt of an overhang about the x-axis.

A protruding portion or lobe 300P2 having a convexly curved surface 300PS may be disposed on a portion of a top surface 300SU of the base element 300L'. A cross-sectional shape of the protruding portion 300P2 parallel to the z-y plane may not be horizontally symmetrical. The protruding portion 300P2 may extend in the y-axis direction (or the widthwise direction of the overhang), and the convexly curved surface 300PS may be a curved surface with any curvature suitable for ensuring a linear interface between the protruding portion 300P2 and the overhang (e.g., the bent overhang OV of FIG. 1C) in the y-axis direction. In another embodiment, although not shown, the surface 300PS of the protruding portion 300P2 may be designed to cause a surface-contact between the protruding portion 300P2 and at least a portion of the overhang. Furthermore, as shown in FIG. 5A, the protruding portion 300P2 may be modified to have a convexly curved surface having an arc shape or an arch shape so that a cross-sectional shape of the protruding portion 300P2 parallel to the y-plane is horizontally symmetrical.

Embodiments of a tilt supporting portion are not limited to the above-described embodiments with reference to FIGS. 5A to 6. In another embodiment, a tilt supporting portion may be a spacer that may function like fulcrum of a lever to cause a tilt of the base element 300L or 300L' to compensate for a tilt of the overhang. For example, a spacer having a fin-like structure may be provided as a fulcrum of a lever on the supporting element 300S, and the center of mass of the base element 300L may be rotatably attached to a top portion of the fin-like structure.

In other words, in another embodiment, a base element 300L may pivot about a rectilinear fulcrum.

Figure 7:
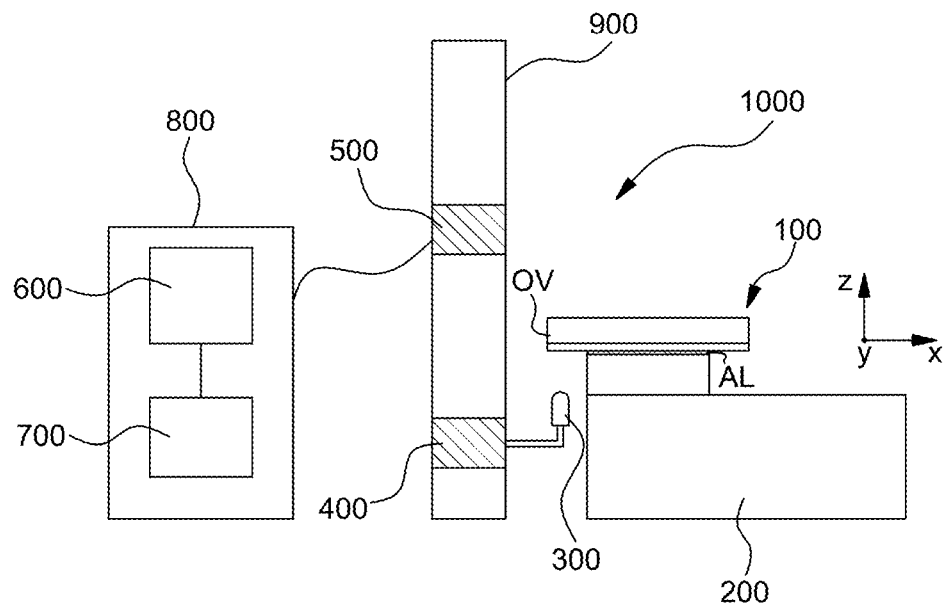
FIG. 7 is a diagram showing an apparatus for measuring an adhesive force of an interlayer adhesive layer, according to an embodiment of the present disclosure.

FIG. 7 is a diagram showing an apparatus 1000 for measuring an adhesive force of an interlayer adhesive layer, according to an embodiment.

Referring to FIG. 7, the apparatus 1000 may include a mounting element 200 fixing a device under test 100, a load applying tip 300 that may contact the bottom surface of an overhang OV to apply a load to the device under test 100 in a tensile mode, a location adjuster 400 moving the load applying tip 300 to apply the load by pushing the bottom surface of the overhang unit OV of the device under test 100 in a predetermined direction (e.g., the z-axis direction), and a load cell 500 detecting a load applied to the load applying tip 300.

In an embodiment, the measurement apparatus 1000 may further include a display 600, which may be a liquid crystal display (LCD) element or an organic/inorganic light-emitting diode (LED) display for displaying information regarding the load applied to the load cell 500. Furthermore, the apparatus 1000 may further include a controller 700 controlling operations of the location adjuster 400, the load cell 500, and the display 600. The display 600 and the controller 700 may be included in a single computer system 800. However, embodiments are not limited thereto. In another embodiment, the controller 700 and the display 600 may be separately located at remote locations, and each of the controller 700 and the display 600 may be a cloud resource consisting of a plurality of electronic devices connected to one another via a network.

The mounting element (or mounting stage) 200 is not limited to a fixed stage. For example, the mounting element 200 may be a stage that is movable in two dimensions (e.g., in the x-axis direction and the y-axis direction) to align the device under test 100 and the load applying tip 300. The load applying tip 300 may include a tiltable structure as described above with reference to FIGS. 5A to 6.

The location adjuster 400 may include a motor like a servo motor for precise location control, a suitable gear like a screw for converting a rotary motion of the motor into a linear motion, and a fixing element like a chuck for fixing the load applying tip 300. The location adjuster 400 may be combined with the load applying tip 300 and moves the load applying tip 300 back and forth, for example, in the z-axis direction, such that the load applying tip 300 contacts or is separated from the bottom surface of the overhang OV of the device under test 100. Therefore, according to an embodiment, adhesive force of the interlayer adhesive layer AL may be measured without fixing the load applying tip 300 to a device under test during measurement of the adhesive force in a tensile mode.

In an embodiment, a location sensor detecting a displacement of the load applying tip 300 may be further provided. For example, the location sensor may be a laser displacement measuring sensor using an array including a laser emitter and a light receiver. Alternatively, an optical image pickup device for observing deformation of the overhang OV may be combined with the apparatus 1000.

The load cell 500 may be fixed to a support 900, e.g., a stand, and may be combined with the load applying tip 300. The load cell 500 may include a transducer that measures a force or a load by converting a physical quantity like a force or a load to electric signals. The transducer may be an elastic element or a strain gauge detecting a magnitude of a load based on a change of an electric signal by using resistance values that vary according to deformation of the elastic element or the strain gauge. The transducer may be a piezoelectric element detecting a magnitude of a load based on a change of an electric signal by using capacitance values that vary according to deformation.

The controller 700 may be hardware, such as an electronic control unit (ECU) or a micro control unit (MCU), software executed on the hardware, or a combination thereof. In an embodiment, the control unit 700 may further include electric circuits configured to amplify a signal and/or filter noise, or the control unit 700 may be connected to a heating apparatus, a temperature detecting sensor, or a humidity sensor arranged outside in order to control environmental conditions such as a temperature or humidity, during measurement of adhesive force of the interlayer adhesive layer AL in a tensile mode. In an embodiment, the controller 700 calculates an energy release rate according to a crack propagation at a bonding interface between an interlayer adhesive layer and one of upper and lower test layers.

FIGS. 8A to 8D are cross-sectional diagrams of stacked semiconductor elements 100K1, 100K2, 100K3, and 100K4 to which a method of measuring an adhesive force of an interlayer adhesive layer AL1, AL2 in a tensile mode may be applied by using overhang OV according to an embodiment of the present disclosure.

Figure 8A:
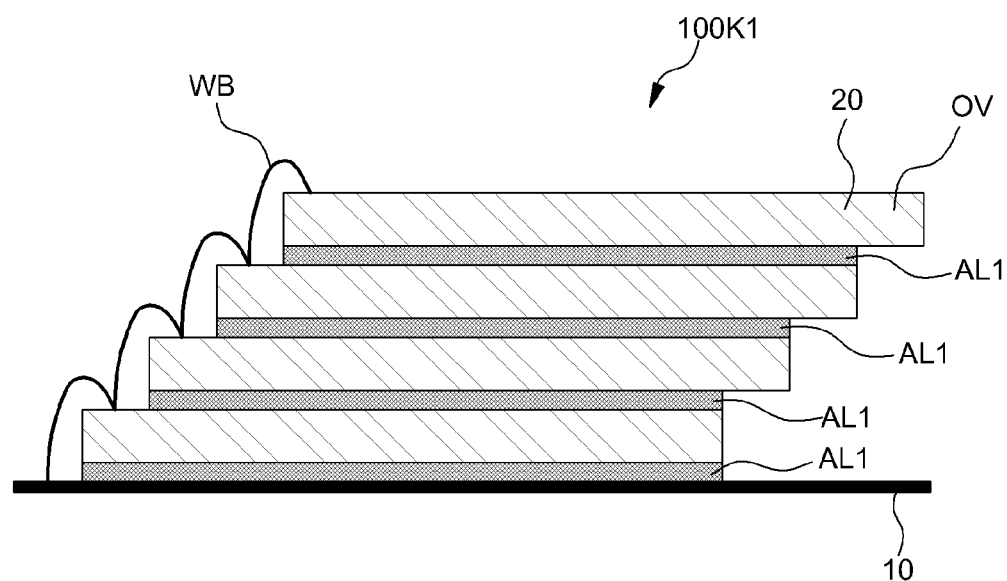
FIGS. 8A to 8D are cross-sectional diagrams of stacked semiconductor devices to which a method of measuring an adhesive force of an interlayer adhesive layer in a tensile mode may be applied by using overhang according to an embodiment.

In the stacked semiconductor structure 100K1 of FIG. 8A, four device layers 20 are stacked on a substrate 10 in a cascading or stepped shape.

Figure 8B:
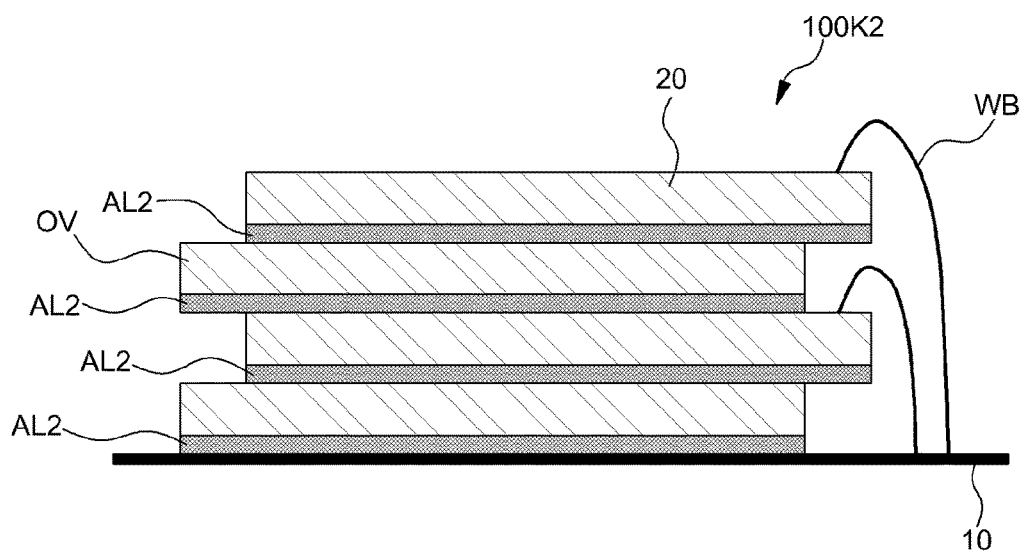

In the stacked semiconductor structure 100K2 of FIG. 8B, the device layers 20 are alternately stacked. In the stacked semiconductor structure 100K3 of FIG. 8C, the device layers 20 are stacked alternately using interposers 25, which are spacer substrates. As a non-limiting example, the interlayer adhesive layer A12 may be a die attach film. The die attach film may be prepared on one of two devices layers to be stacked adjacent to each other in advance of sawing or cutting a processed wafer or encapsulated intermediate package structure to fabricate the singulated devices layers 20, for example, chips or packages.

Figure 8C:
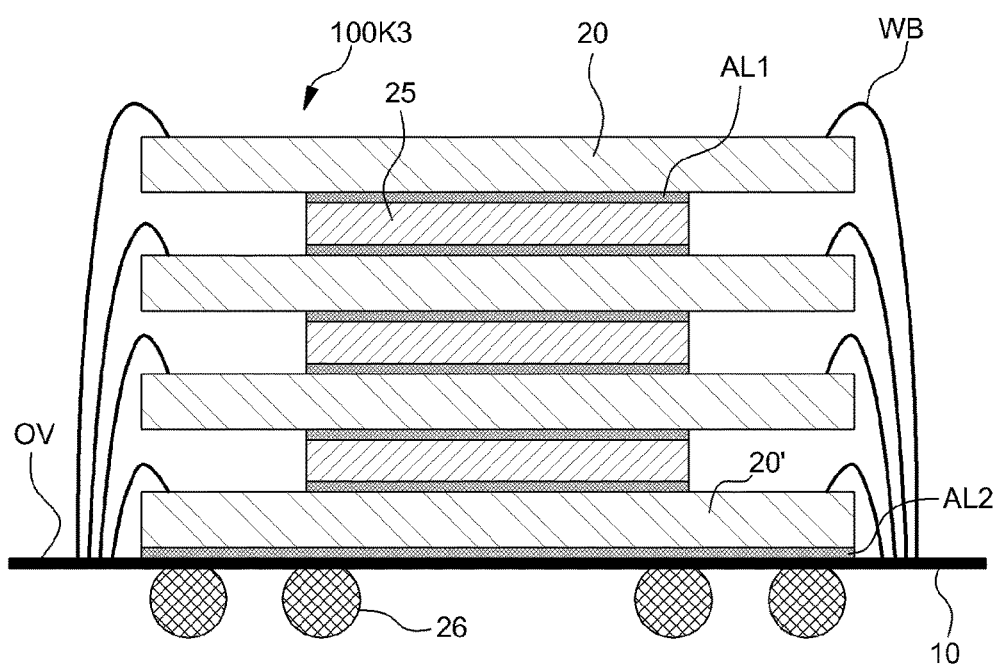

In the stacked semiconductor structure 100K3 of FIG. 8C, the reference numeral 26 denotes electrodes (e.g., solder balls) connecting the stacked semiconductor structure 100K3 to an external circuit. The device layers 20, 20' are stacked or stacked using interposers 25 such that the device layers 20 and 20' expose electrode pads that are connected to each other by wires WB. As a non-limiting example, a lower device layer 20' may be disposed via die attach film AL2 on the substrate by using a flipped die stacking technique. In an example, the lower device layer 20' may include any suitable via conductor, for example, a through silicon via for connecting the device layer to the conductive wire WB.

Figure 8D:
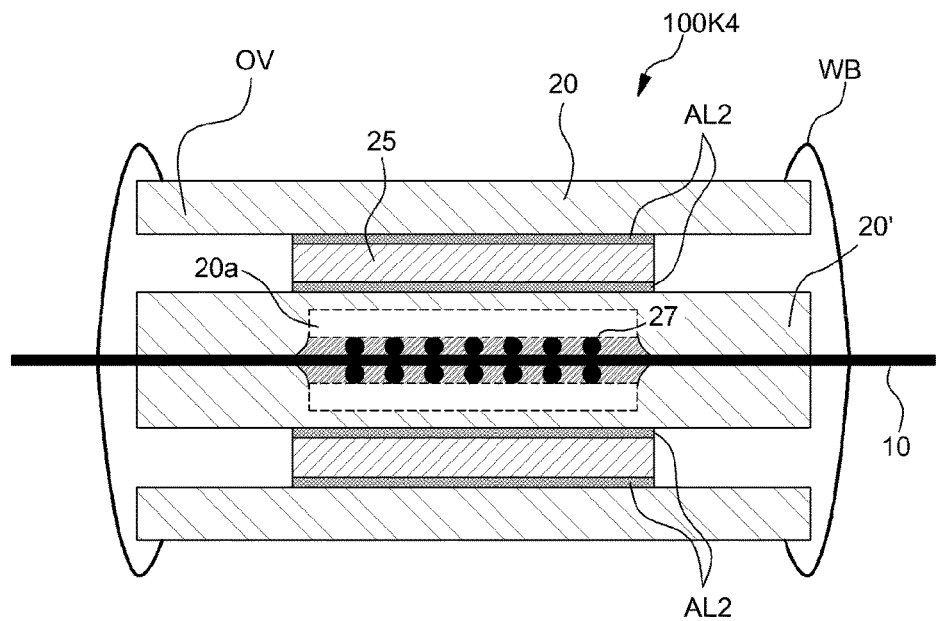

In another example, in the stacked semiconductor structure 100K4 of FIG. 8D, device layers 20 may be stacked on both sides of the substrate 10. In one embodiment, a lower device layer 20' may be provided with a flipped chip 20a mounted on the substrate 10 by using a flip-chip technique.

According to various embodiments of the present invention, any feature, structure or stack method of the above set forth examples disclosed by referring to FIG. 8A to 8D, may be implemented independently or in combination of other feature, structure or stack method, and the embodiments of the present invention should not be construed as being limited to the embodiments in the FIG. 8A to 8D. In various embodiments according to the present invention, at least one overhang OV may be provided by at least one device layers 20 and 20' or the substrate 10 such that the measurement of adhesive force of the interlayer adhesive layer AL1 or AL2 in a tensile mode may be performed by using the at least one overhang OV.

Measurement of adhesive force of the interlayer adhesive layer AL1 or AL2 in a tensile mode according to an embodiment may be utilized for product inspection based on a pass/fail test, for example, by sampling some of pre-wire bonding stacked semiconductor structures obtained from the illustrated stacked semiconductor structures 100K1, 100K2, 100K3, and 100K4. In another embodiment, a device under test for measuring adhesive force of the interlayer adhesive layer AL1 or AL2 in a tensile mode may be prepared as a test vehicle that has dimensions identical or similar to those of final semiconductor devices. Embodiments are not limited to the above-described stacked semiconductor structures, and various modifications may be possible by reflecting various factors including form factor reduction, power consumption reduction, etc. For example, stacked semiconductor devices may not be limited to have electric connections using a wire bonding, but may have 3-dimensional stacked structures using a through silicon via (TSV).

Hereinafter, characteristics and beneficial aspects of the present disclosure will be described based on embodiments selected from among the above-described embodiments. The below descriptions are merely for illustrative purposes, and embodiments of the present disclosure are not limited thereto.

EXPERIMENTAL EXAMPLES

Two silicon chips were prepared as a lower test layer and an upper test layer of each of three test groups DUT A1-DUT A5; DUT B1-DUT B5; and DUT C1-DUT C5, each of which includes 5 devices under test. The silicon chips were rectangular chips formed by performing a backside grinding process on the silicon wafer to reduce a thickness of a silicon wafer to 550 μm and by cutting the polished silicon wafer into chips each having a size of 9.6 mm×15.2 mm. A polyimide passivation layer having a thickness of 4.5 μm was applied to the top surface of the silicon chip, which is an active surface. A lower test layer was mounted on a printed circuit board, and an upper test layer was rotated by 90° and then stacked on the lower test layer. As a result, an overhang was provided on the upper test layer. The upper and lower test layers were combined with each other by using a die attach film and were thermally hardened at 150° C. for 2 hours.

After the stacked device under test was separated from the printed circuit board, the device under test was turned upside down and adhered to an aluminum block, which corresponds to a mounting element, by using the SCOTCH-WELD™ epoxy adhesive sold by 3M. For activation of the epoxy adhesive, a thermal hardening operation was performed at 60° C. for about four hours. As a result, a plurality of devices under test were fabricated.

Thicknesses of die attach films each disposed between a corresponding lower test layer and a corresponding upper test layer of the respective devices under test were 20 μm (DUT A1-DUT A5), 10 μm (DUT B1-DUT B5), and 5 μm (DUT C1-DUT C5). Adhesive force of the die attach films was measured at the room temperature (25° C.). Mechanical properties of the die attach films were measured by using EXSTAR 6000, a dynamic mechanical analyzer available by Seiko. An elastic modulus and a Poisson's ratio of the die attach films are 1.05 GPa and 0.3, respectively, and a glass transition temperature of the die attach films is 43° C. Material anisotropy of the silicon chips was simplified by assuming an isotropic material that has mechanical properties when a (100) wafer is bent in a direction of [110], where an elastic modulus and a Poisson's ratio of the silicon chips are 169 GPa and 0.064, respectively.

A load applying tip 300A having a tiltable structure as shown in FIG. 5A was used. The protruding portion 300P1 of the base element 300L of the load applying tip 300A had a semi-cylindrical shape with a radius of about 0.75 mm. The base element 300L may have a height (e.g., in the z-direction) of about 3.5 mm and a width (e.g., in the x-direction) of about 3.0 mm to have a sufficient rigidity during application of a load. The load applying tip 300A moves in a vertically upward direction (e.g., in the z-direction) and applied a load to the bottom surface of the overhang of the device under test, where the load was applied at a speed of 10 μm/sec.

Figure 9:
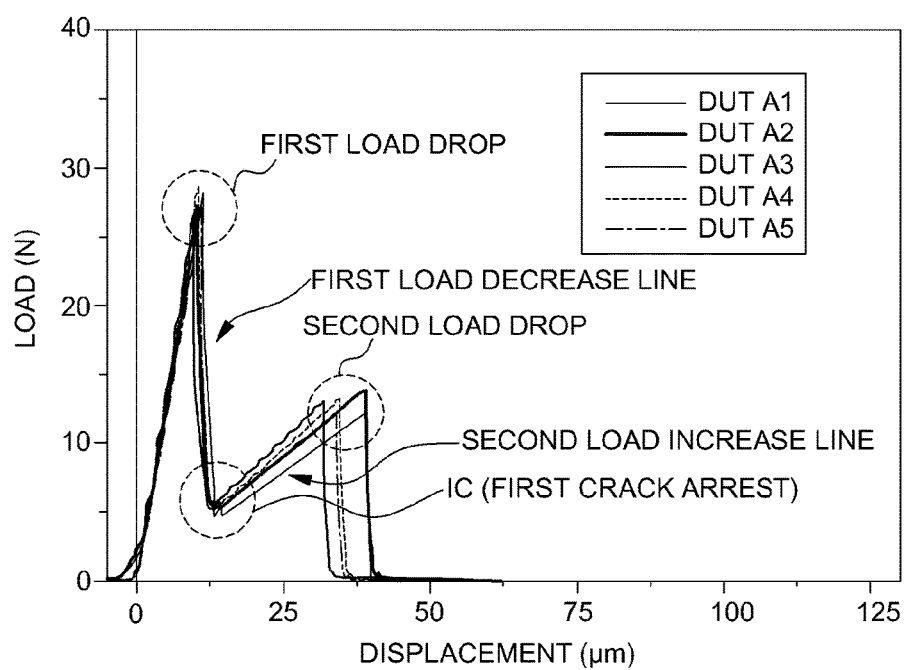
FIG. 9 is a graph showing load-displacement curves of five devices under test, each of which includes a die attach film having a thickness of 20 μm, according to an embodiment.

FIG. 9 is a graph showing load-displacement curves of five devices under test DUT A1-DUT A5, each of which includes a die attach film having a thickness of 20 μm, according to the experimental example. A value of the x-axis corresponds to a displacement of a load applying tip, whereas a value of the y-axis corresponds to a magnitude of an applied load.

Referring to FIG. 9, an applied load linearly increases as the load applying tip moves, while two load drops were observed. The first load drop, or non-recoverable strain, was observed at the load of 28 N and the displacement of about 11 μm, and may indicate an occurrence of a crack at a bonding interface. As the displacement increased thereafter, the crack propagated at the bonding interface, and a second elastic slope was observed. Next, the second load drop was observed, and the crack at the bonding interface propagates further. The second load drop may be due to an occurrence of a crack in the overhang, which results from a significant deformation or a plastic deformation of an interlayer adhesive layer.

Adhesive force of an interlayer adhesive layer in a tensile mode may be defined as an energy release rate during a crack initiation or a crack arresting time. However, in case of an actual device under test, an energy release rate during the crack initiation may reflect not only adhesive force of an interface, but also plasticity-related factors. Therefore, an energy release rate measured during the crack arresting time may be more suitable for determining the adhesive force of an interlayer adhesive layer in a tensile mode than an energy release rate measured during the crack initiation.

Furthermore, the crack initiation and crack arrest may occur only once or more than once depending on various parameters including a thickness or a size of an interlayer adhesive layer. Thus, for standardization of quantitative measurement, adhesive force of the interlayer adhesive layer may be defined as an energy release rate at a first crack arresting time, which is a time when an initial crack arrest occurs.

In an embodiment, adhesive force of an interlayer adhesive layer in a tensile mode may be defined as an energy release rate at a crack initiation time. In an embodiment, the adhesive force in the tensile mode may be defined as an energy release rate at a crack arresting time. More specifically, the adhesive force in the tensile mode may be defined as an energy release rate at an initial crack arresting time (or a first crack arresting time). Determining the initial crack arresting time will be described below in more detail.

Table 1 shows values of compliances, lengths, and energy release rates measured from the devices under test DUT A1-A5, each including the die attach film having 20 μm thickness. Referring to Table 1, a crack length may be determined according to Equation 2 and a measured compliance value. A critical load (referred to as the reference character 'Pc' in Equation 1) at a crack arresting time may be obtained from a point of intersection between a load decrease line and a follow-up compliance line. For example, when an intersection point IC between a first load decrease line and a second load increase line is obtained, the value of the load at the intersection point IC corresponds to an initial critical load or initial energy release rate at a first crack arresting time. Next, an energy release rate may be calculated according to Equation 5 above.

TABLE 1

| Device under test | First crack Initiation | | | First crack Arrests | | |
|---|---|---|---|---|---|---|
| | Compliance ($10^{-3}$ mm/N) | Crack Length (mm) | Energy Release Rate (mJ/mm$^2$) | Compliance ($10^{-3}$ mm/N) | Crack Length (mm) | Energy Release Rate (mJ/mm$^2$) |
| DUT A1 | 0.251 | 2.152 | 11.904 | 6.127 | 7.392 | 2.855 |
| DUT A2 | 0.175 | 1.837 | 8.959 | 5.198 | 6.966 | 2.936 |
| DUT A3 | 0.177 | 1.845 | 8.809 | 4.399 | 6.557 | 2.836 |
| DUT A4 | 0.184 | 1.881 | 9.804 | 4.908 | 6.823 | 2.892 |
| DUT A5 | 0.247 | 2.135 | 11.329 | 5.185 | 6.960 | 2.858 |
| Average | 0.207 | 1.970 | 10.161 | — | — | 2.875 |
| Standard Deviation | 0.039 | 0.159 | 1.396 | — | — | 0.039 |
| Coefficient of Variation (CV) | 0.187 | 0.081 | 0.137 | — | — | 0.014 |

Referring to Table 1, an average value of energy release rates at corresponding first crack arresting times was 2.875 mJ/mm$^2$. Small values of a standard deviation (i.e., 0.039) and a coefficient of variation CV (i.e., 0.014) of the energy release rates at the first crack arresting times indicate that the measurement of the adhesive force is reliably performed. A crack length varies within a range from about 6.56 mm to about 7.39 mm. An average value of energy release rates at corresponding first crack initiation times is 10.161 mJ/mm$^2$, which is significantly greater than the average value of the energy release rates at the first crack arresting times. The reason why higher energy release rates measured at the first crack initiation times than those measured at the first crack arresting times is that additional energy release rates caused by plastic deformation of the devices under tests affects accumulatively the measured energy release rates at the first crack initiation times. Furthermore, a CV value of the energy release rates at the first crack initiation times is about 8.7 times greater than a CV value of the energy release rates at the first crack arresting times.

Figure 10:
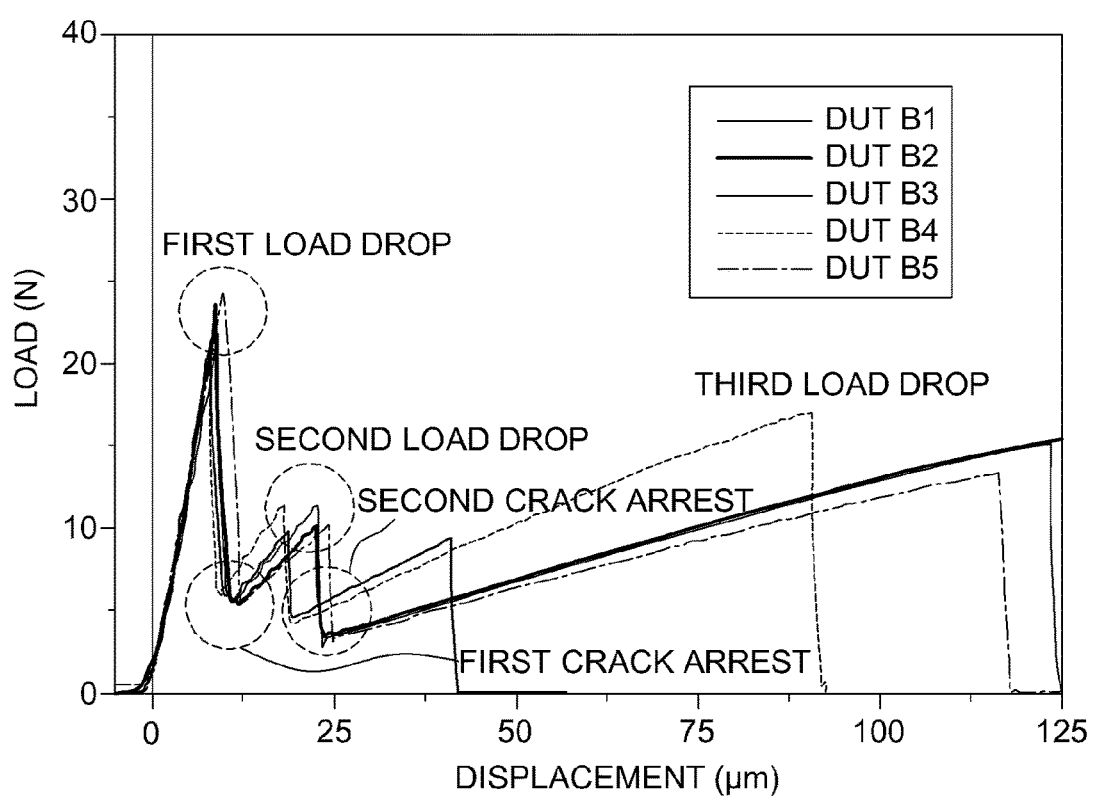
FIG. 10 is a graph showing load-displacement curves of five devices under test, each of which includes a die attach film having a thickness of 10 μm, according to an embodiment.

FIG. 10 is a graph showing load-displacement curves of five devices under test DUT B1-DUT B5, each of which includes a die attach film having a thickness of 10 μm, according to an embodiment. Table 2 shows compliances, lengths, and energy release rates measured from the devices under test DUT B1-DUT B5.

Referring to FIG. 10, three load drops were observed. Compared to the load drops of FIG. 9, the peaks of the first load drops are lower, and crack lengths at the first crack initiation times are smaller. Referring to Table 2, an average value of the energy release rates at corresponding first crack arresting times is 2.48 mJ/mm$^2$, which is smaller than that of the devices under test DUT A1-DUT A5 of FIG. 9. An average value of energy release rates at corresponding second crack arresting times is 2.53 mJ/mm$^2$, which is almost identical to that at the first crack arresting times.

TABLE 2

| Device under test | First crack Initiation | | | First crack Arrests | | | Second crack Arrests | | |
|---|---|---|---|---|---|---|---|---|---|
| | Compliance | Length | Adhesive force | Compliance | Length | Adhesive force | Compliance | Length | Adhesive force |
| DUT B1 | 0.270 | 2.307 | 7.106 | 3.267 | 5.968 | 2.376 | 14.194 | 10.063 | 2.323 |
| DUT B2 | 0.230 | 2.159 | 7.408 | 3.897 | 6.360 | 2.620 | 14.374 | 10.107 | 2.426 |
| DUT B3 | 0.214 | 2.095 | 5.865 | 2.953 | 5.753 | 2.337 | 8.298 | 8.330 | 2.813 |
| DUT B4 | 0.161 | 1.860 | 4.356 | 2.612 | 5.502 | 2.450 | 9.082 | 8.600 | 2.658 |
| DUT B5 | 0.285 | 2.358 | 9.110 | 4.322 | 6.602 | 2.631 | 15.680 | 10.419 | 2.405 |
| Average | 0.232 | 2.156 | 6.769 | — | — | 2.483 | — | — | 2.525 |
| Standard Deviation | 0.049 | 0.197 | 1.778 | — | — | 0.137 | — | — | 0.203 |
| Coefficient of Variation (CV) | 0.211 | 0.091 | 0.263 | — | — | 0.055 | — | — | 0.081 |

Figure 11:
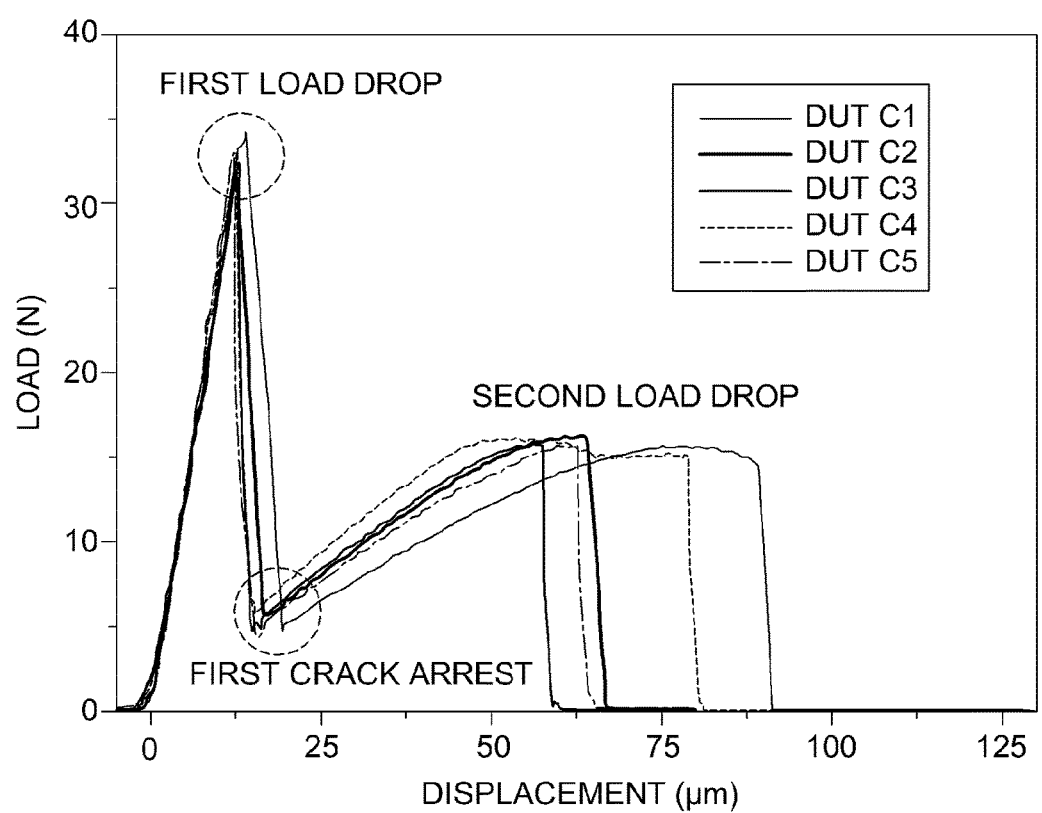
FIG. 11 is a graph showing load-displacement curves of five devices under test, each of which includes a die attach film having a thickness of 5 μm, according to an embodiment.

FIG. 11 is a graph showing load-displacement curves of five devices under test DUT C1-DUT C5, each of which includes a die attach film having a thickness of 5 μm, according to an embodiment. Table 2 shows compliances, lengths, and energy release rates measured from the devices under test DUT C1-DUT C5.

Referring to FIG. 11, similarly to the devices under test DUT A1-DUT A5 of FIG. 9, two load drops were observed. However, a relatively high load of about 35 N at first load drops and a higher average value of energy release rates of 3.51 mJ/mm$^2$ were observed at corresponding first crack arresting times. Furthermore, a significant nonlinear behavior was observed before the second load drops occurred.

TABLE 3

| Device under test | First crack Initiation | | | First crack Arrests | | |
|---|---|---|---|---|---|---|
| | Compliance ($10^{-3}$ mm/N) | Length (mm) | Adhesive force (mJ/mm$^2$) | Compliance ($10^{-3}$ mm/N) | Length (mm) | Adhesive force (mJ/mm$^2$) |
| DUT C1 | 0.244 | 2.298 | 15.635 | 7.358 | 8.064 | 3.492 |
| DUT C2 | 0.220 | 2.205 | 12.752 | 6.057 | 7.530 | 3.531 |
| DUT C3 | 0.216 | 2.190 | 13.498 | 5.889 | 7.456 | 3.559 |
| DUT C4 | 0.124 | 1.746 | 9.784 | 5.311 | 7.189 | 3.544 |
| DUT C5 | 0.135 | 1.806 | 10.254 | 6.515 | 7.726 | 3.440 |
| Average | 0.188 | 2.049 | 12.385 | — | — | 3.513 |
| Standard Deviation | 0.055 | 0.254 | 2.411 | — | — | 0.048 |
| Coefficient of Variation (CV) | 0.290 | 0.124 | 0.195 | — | — | 0.014 |

In the experimental examples described above with reference to FIGS. 9 to 11, crack lengths of the three types of devices under test were calculated from compliances measured by applying the Winkler foundation model. Two or three load drops were observed, and adhesive force measured at first crack arresting times were 2.88 mJ/mm$^2$, 2.48 mJ/mm$^2$, and 3.51 mJ/mm$^2$ for the devices under test including die attach films having thicknesses of 20 μm, 10 μm, and 50 μm, respectively. As described above, according to an embodiment of the present disclosure, a method of measuring adhesive force in a tensile mode enables measurement of adhesive force of an interlayer adhesive layer in the tensile mode independently of crack lengths.

As shown in the experimental examples above, an energy release rate Gc may be measured at a crack arresting time so that adverse effects, such as a nonlinear deformation or a plastic deformation, may not be significant. Furthermore, an energy release rate may be measured at a first crack arresting time. According to the embodiments of the present disclosure, a method of measuring adhesive force in a tensile mode enables measurement of adhesive force of an interlayer adhesive layer in the tensile mode independently of crack lengths.

In exemplary embodiments of the present invention, adhesive force and reliability of an interlayer adhesive layer in a tensile mode are determined by providing an overhang at an upper test layer of a device under test, applying a load to an exposed bottom surface of the overhang in a vertical direction, and calculating an energy release rate based on a crack propagation at the bonding interface between the upper test layer and a lower test layer. Therefore, adhesive force and reliability of the interlayer adhesive layer may be quantitatively measured by applying a load to the bottom surface of the overhang, without mechanically fixing a separate jig onto to the top surface of the upper test layer. Furthermore, a device under test including an upper test layer with an overhang may be an intermediate structure formed during a process of fabricating a common stacked semiconductor package or may be fabricated using a conventional semiconductor package fabricating process. Therefore, a method of quantitatively measuring adhesive force in a tensile mode with excellent process compatibility is provided by this disclosure.

Furthermore, according to another embodiment of the present disclosure, an apparatus for quantitatively measuring adhesive force and reliability of an interlayer adhesive layer for a stacked semiconductor element having the above-stated beneficial aspects may be provided.

While the present disclosure has been particularly shown and described with reference to embodiments thereof, it will be understood by those of ordinary skill in the art that various changes in form and details may be made.

What is claimed is:

1. A method of measuring an adhesive force of an interlayer adhesive layer for a stacked semiconductor device, the method comprising:
   providing a device under test, the device under test comprising:
      a lower test layer;
      an upper test layer stacked on the lower test layer and including an overhang that protrudes past an edge of the lower test layer by a predetermined length; and
      the interlayer adhesive layer disposed between the lower test layer and the upper test layer and bonded to the lower test layer and the upper test layer;
   fixing the lower test layer onto a mounting stage; and
   measuring the adhesive force of the interlayer adhesive layer in tensile mode by applying a load to a bottom surface of the overhang of the upper test layer in a first direction.

2. The method of claim 1, wherein each of the lower test layer and the upper test layer is a device layer, a substrate, two or more stacked device layers, two or more stacked substrates, or a stacked structure including one or more device layers and one or more substrates.

3. The method of claim 2, wherein the device layer comprises a semiconductor chip, a semiconductor die, a wafer, an encapsulated package, or a combination thereof, and
   wherein the substrate comprises a wafer, a lead frame, a die paddle, an interposer, a printed circuit board, a flexible printed circuit board, a film-type wire, or a combination thereof.

4. The method of claim 1, wherein the interlayer adhesive layer comprises an adhesive film or an adhesive paste.

5. The method of claim 1, wherein the device under test is an intermediate structure from a fabrication process of a semiconductor package, the semiconductor package comprising a plurality of device layers of a same type or of different types.

6. The method of claim 1, wherein providing the device under test comprises:
   performing any one of a rotation process, a translation process, a flip process, and a combination thereof to a first test layer and a second test layer, such that one of the first and second test layers corresponds to the upper test layer and the other of the first and second test layers corresponds to the lower test layer.

7. The method of claim 1, wherein the bottom surface of the overhang of the upper test layer corresponds to a surface of a passivation layer or a reinforcement layer.

8. The method of claim 1, wherein the device under test has a wedge structure such that a length of the lower test layer in a second direction is greater than a length of the overhang of the upper test layer in the second direction, the second direction being perpendicular to the first direction.

9. The method of claim 1, wherein the load is applied by a load applying tip, and
wherein the load applying tip comprises a protruding portion, the protruding portion including a convexly curved surface that contacts the bottom surface of the overhang during the application of the load.

10. The method of claim 9, wherein a contact interface between at least a portion of the convexly curved surface and the bottom surface of the overhang is a linear contact interface that extends in a second direction, the second direction corresponding to a lengthwise direction of the overhang.

11. The method of claim 10, wherein, the base is tilted around an axis of rotation in a third direction perpendicular to the first and second directions, the third direction corresponding to a propagation direction of crack in the interlayer adhesive layer.

12. The method of claim 10, wherein the load applying tip further comprises:
a tilt supporting portion disposed between the support and the base and separating the support and the base from each other; and
a trench accommodating the tilt supporting portion and allowing the tilt supporting portion to rotate about the axis of rotation to tilt the base, the trench being provided on either the support or the base.

13. The method of claim 12, wherein a cross-section of the tilt supporting portion has an arc shape or a circular shape with a first curvature, the cross-section being perpendicular to a third direction, the third direction being perpendicular to the first and second directions and corresponding to a widthwise direction of the overhang, and
wherein the trench has a second curvature identical to the first curvature of the tilt supporting portion.

14. The method of claim 12, wherein the tilt supporting portion and the trench extend in the third direction.

15. The method of claim 1, wherein the load is applied by a load applying tip,
wherein the load applying tip comprises a support and a base, the base being mounted on the support,
wherein the base contacts the bottom surface of the overhang, and
wherein the base is tilted according to a tilt of the overhang.

16. The method of claim 1, wherein measuring the adhesive force comprises calculating an energy release rate according to a crack propagation at a first bonding interface of the interlayer adhesive layer and the upper test layer, a second bonding interface of the interlayer adhesive layer and the lower test layer, or both.

17. The method of claim 16, wherein the energy release rate is calculated at a crack initiation time or a crack arresting time.

18. The method of claim 16, wherein the adhesive force in the tensile mode is defined by an energy release rate at a first crack arresting time, the method further comprising:
obtaining a load-displacement graph that includes a first load increase line, a load decrease line, and a second load increase line, the load decrease line being subsequent to the first load increase line, the second load increase line being subsequent to the load decrease line; and
determining an intersection point between the load decrease line and the second load increase line, the intersection point corresponding to the first crack arresting time.

* * * * *